(12) United States Patent
Yang et al.

(10) Patent No.: US 8,227,417 B2
(45) Date of Patent: Jul. 24, 2012

(54) HMGN POLYPEPTIDES AS IMMUNE ENHANCERS AND HMGN ANTAGONISTS AS IMMUNE SUPPRESSANTS

(75) Inventors: De Yang, Frederick, MD (US); Joost J. Oppenheim, Bethesda, MD (US); Michael Bustin, Rockville, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 277 days.

(21) Appl. No.: 12/509,088

(22) Filed: Jul. 24, 2009

(65) Prior Publication Data
US 2010/0021488 A1    Jan. 28, 2010

Related U.S. Application Data

(60) Provisional application No. 61/083,781, filed on Jul. 25, 2008.

(51) Int. Cl.
*A61K 38/19* (2006.01)
(52) U.S. Cl. ........................................ 514/19.3; 514/2.4
(58) Field of Classification Search ........................ None
See application file for complete search history.

(56) References Cited

U.S. PATENT DOCUMENTS

| | | | |
|---|---|---|---|
| 6,743,619 B1 | 6/2004 | Tang et al. | |
| 2004/0156851 A1 | 8/2004 | Newman | |
| 2006/0121047 A1 | 6/2006 | Tracey | |
| 2007/0154529 A1 * | 7/2007 | Bullerdiek | 424/445 |

FOREIGN PATENT DOCUMENTS

| | | |
|---|---|---|
| WO | WO 03/054152 A2 | 7/2003 |
| WO | WO 2004/061456 A2 | 7/2004 |
| WO | WO 2004/083398 A2 | 9/2004 |
| WO | WO 2005/049806 A2 | 6/2005 |
| WO | WO 2006083301 A2 * | 8/2006 |

OTHER PUBLICATIONS

Hock et al., TRENDS in Cell Biology, vol. 17 No. 2, pp. 72-79 (2006).*
Shirakawa et al., JBC, vol. 275, No. 9, Issue of Mar. 3, pp. 6368-6374, 2000.*
Rouhiainen et al., J. Leukoc. Biol. 81: 49-58; 2007.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Bork et al., 1996, Trends in Genetics 12:425-427.*
Brenner, 1999, Trends in Genetics 15:132-133.*
Smith et al., 1997, Nature Biotechnology 15:1222-1223.*
Doerks et al., 1998, Trends in Genetics 14:248-250.*
Skolnick et al., 2000, Trends in Biotech. 18(1):34-39.*
Saleh et al., Current Pharmaceutical Design, 2005, vol. 11, No. 27, pp. 3461-3473.*
Strom et al., Therapeutic Immunology edited by Austen et al., Blackwell Science, Cambridge, MA, 1996; pp. 451-456.*
Gu et al., Vaccine 25 (2007) 526-534.*
Ueda et al., Mol. Cell. Biol. 2008, 28(9):2872.*
Ayer et al., *Arthritis & Rheumatism*, 37 (1), 98-103 (1994).
Choi et al., *Mol. Biotechnol.*, 31, 193-202 (2005).
Hudecz, *Methods Mol. Biol.*, 298, 209-223 (2005).
Kirin et al., *Inorg Chem.*, 44 (15), 5405-5415 (2005).
Yang et al. Presentation at the 3rd Advances Against Aspergillosis (AAA) Conference (Jan. 16, 2008).

* cited by examiner

*Primary Examiner* — Zachary Skelding
(74) *Attorney, Agent, or Firm* — Leydig, Voit & Mayer, Ltd.

(57) ABSTRACT

A method of enhancing an antigen-specific immune response in a host comprising administering to the host an HMGN polypeptide comprising at least one of HMGN1, HMGN3a, HMGN3b, HMGN4, Nsbp1, or a functional fragment thereof, in an amount effective to enhance an antigen-specific immune response; as well as a pharmaceutical composition comprising an HMGN polypeptide comprising at least one of HMGN1, HMGN3a, HMGN3b, HMGN4, Nsbp1, or a functional fragment thereof, and an antigen, or nucleic acids encoding such molecules; and related methods and compositions.

32 Claims, 11 Drawing Sheets

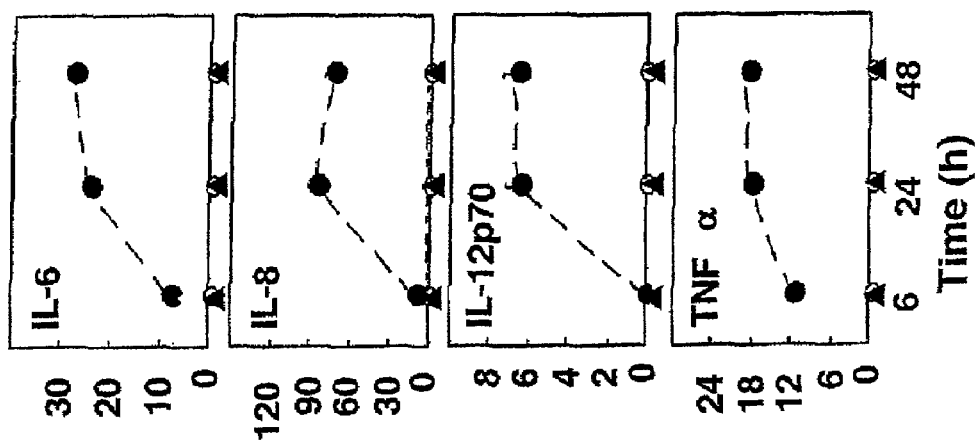
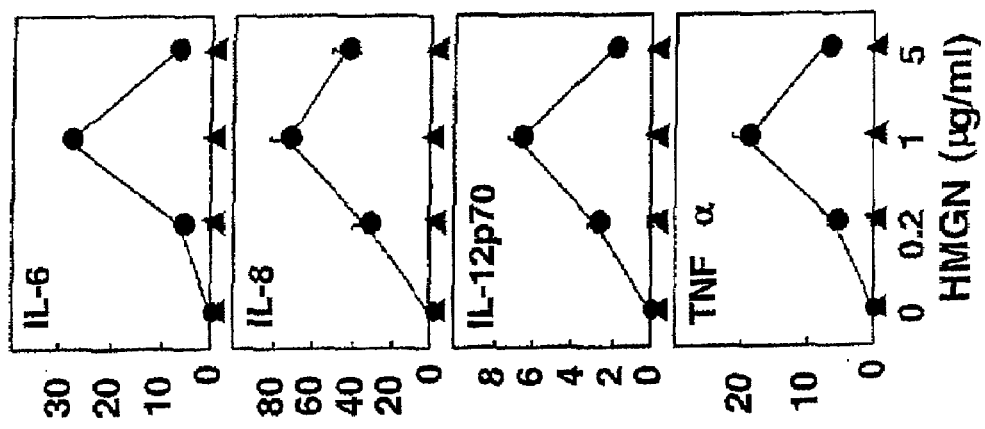

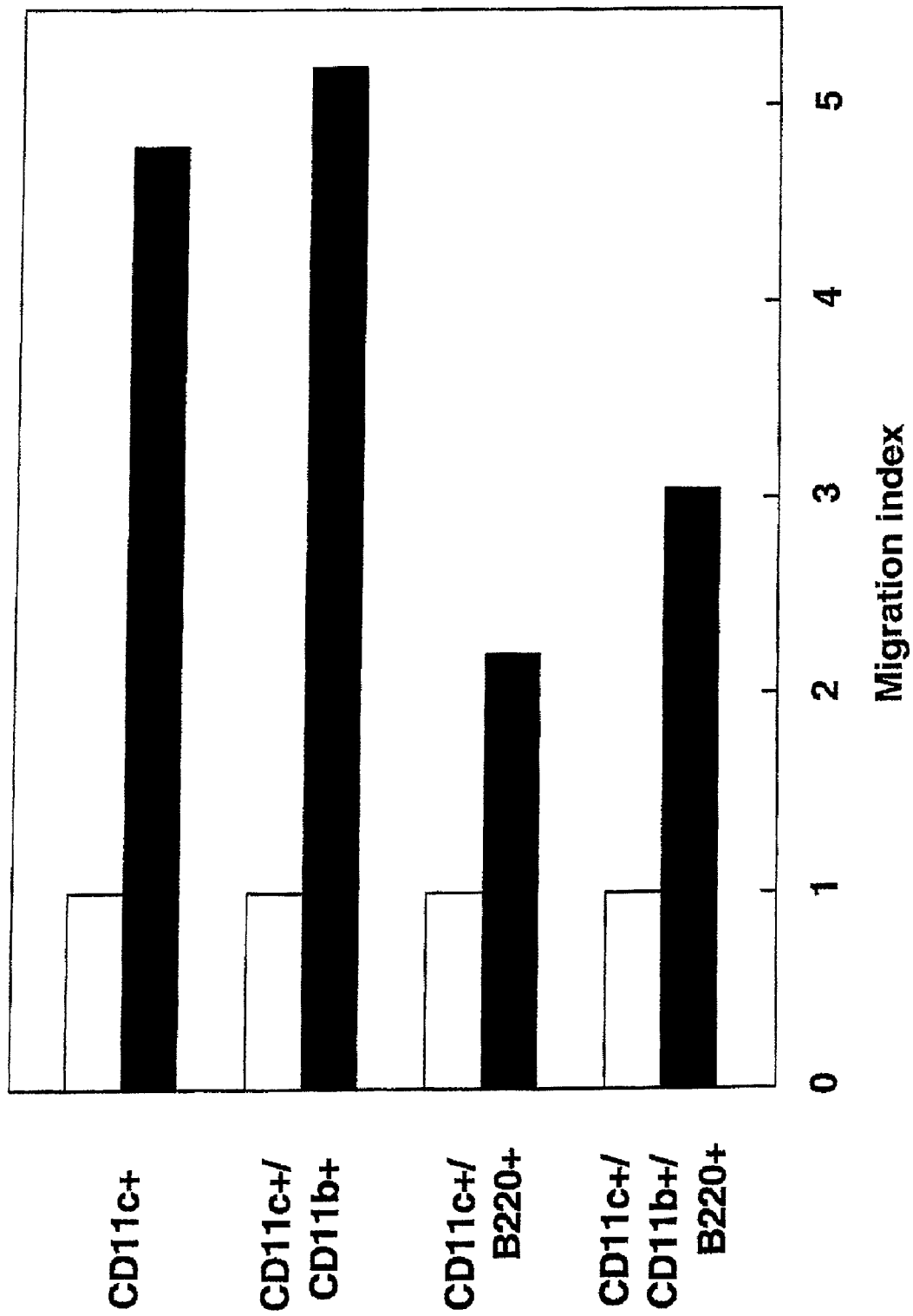

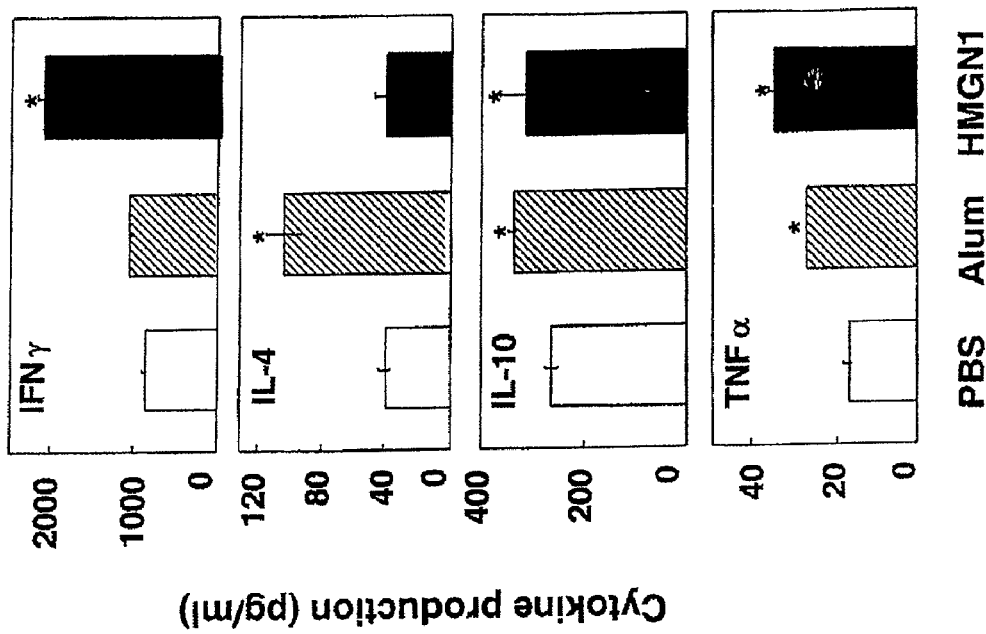
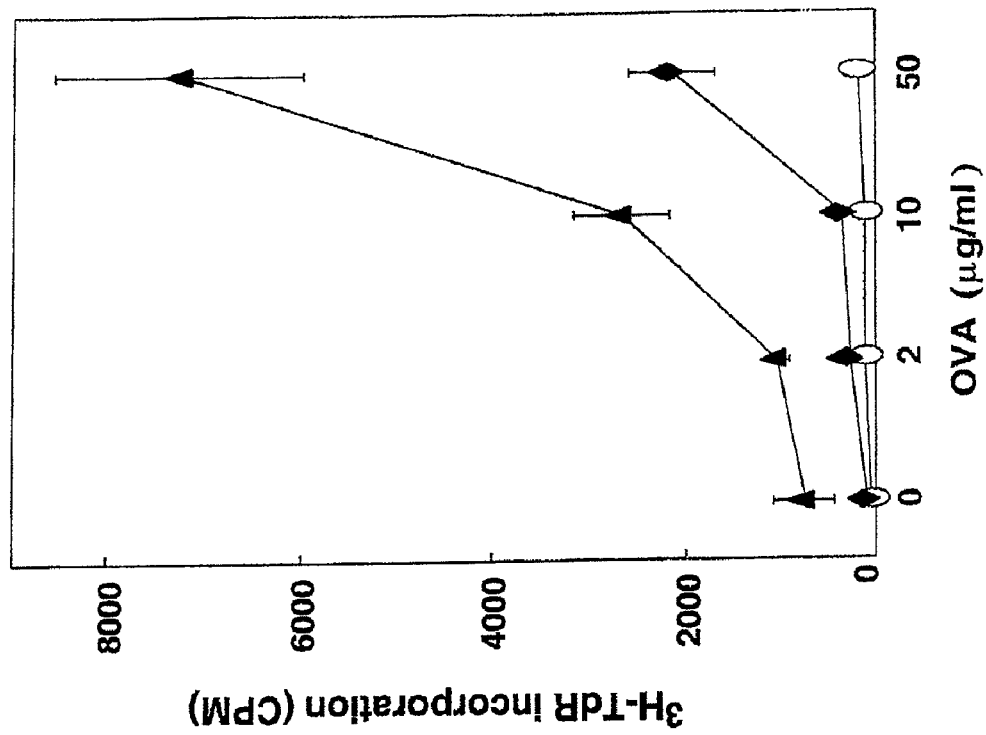

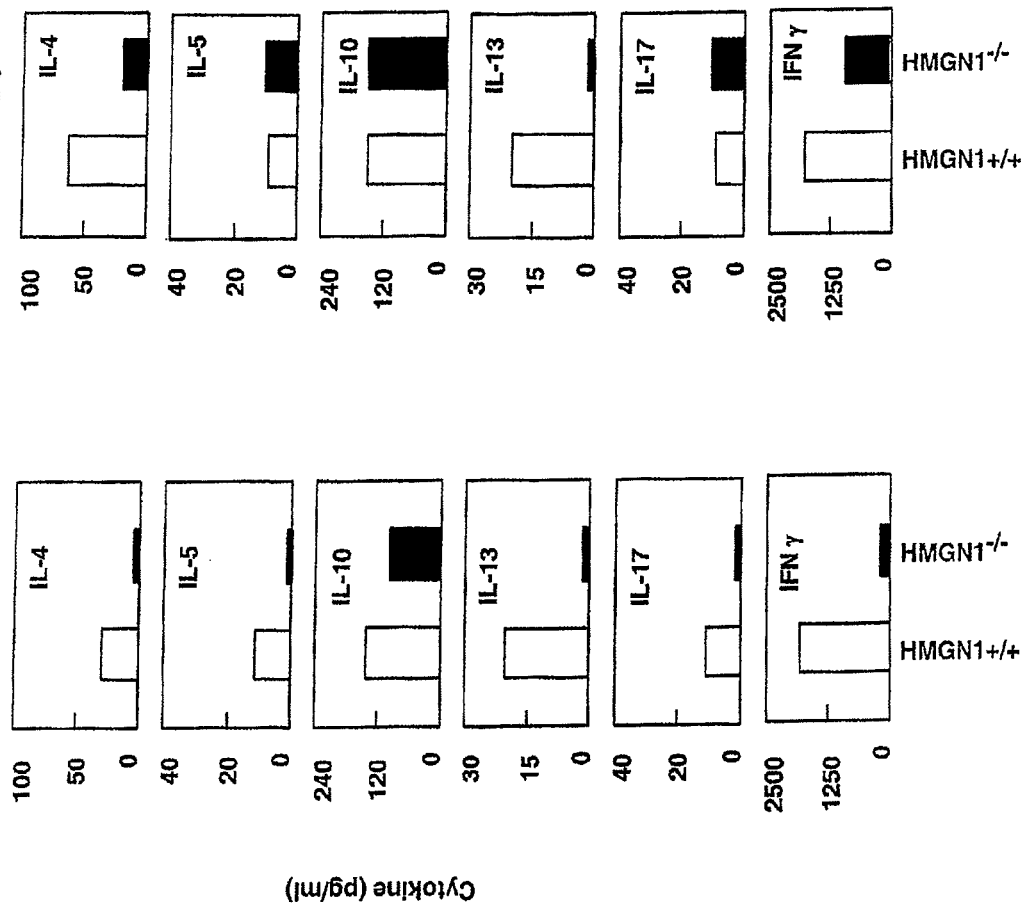

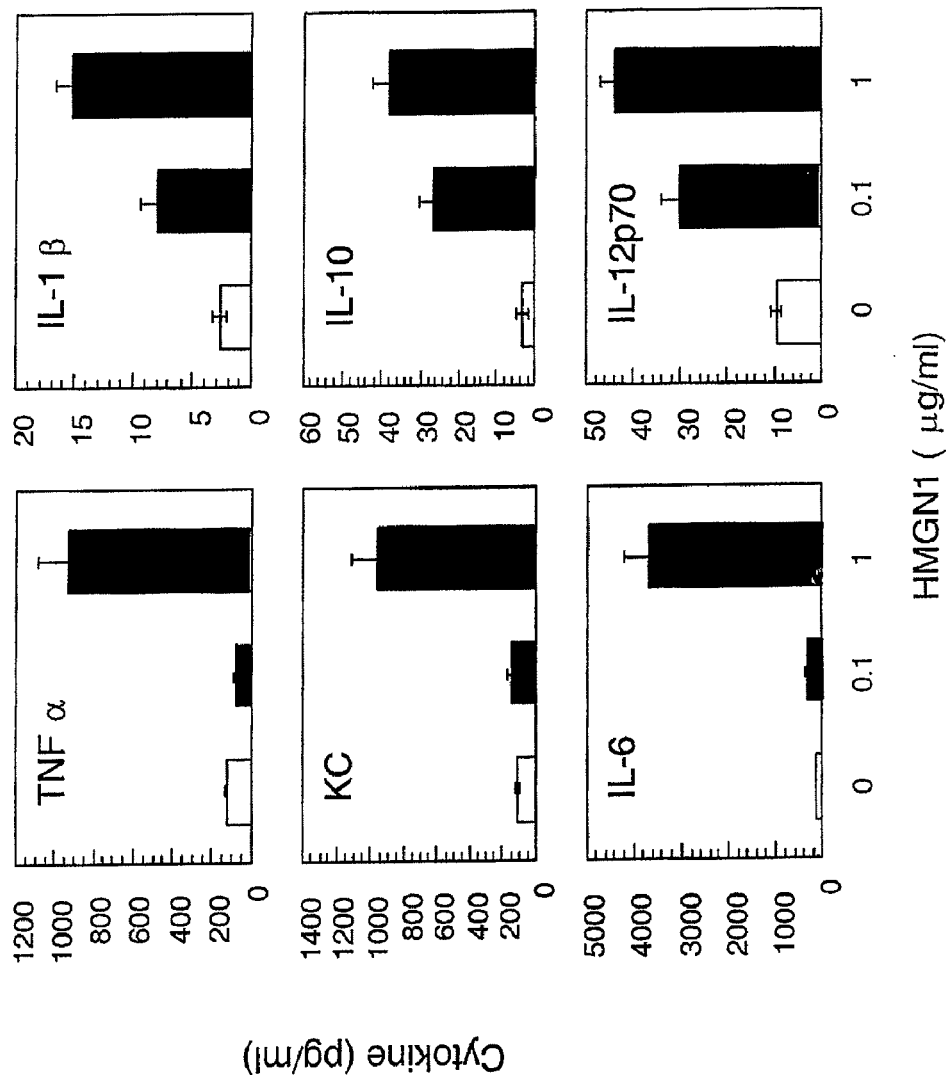

HMGN POLYPEPTIDES AS IMMUNE ENHANCERS AND HMGN ANTAGONISTS AS IMMUNE SUPPRESSANTS

BACKGROUND OF THE INVENTION

HMGN polypeptides belong to the high mobility group (HMG) family of chromosomal binding peptides. HMGN polypeptides typically function inside the cell nucleus to bind to DNA and nucleosomes and regulate the transcription of various genes. HMGN polypeptides also can be released by peripheral blood mononuclear cells.

A patient's immune response often plays an important role in the progression of disease and the effectiveness of medical treatments for disease. Two types of immune responses can occur in a patient: a Th-1 pro-inflammatory type and a Th-2 anti-inflammatory type. The Th-1 (cell-mediated) type of immune response activates T-cells and macrophages, while the Th-2 (antibody-mediated) type of immune response activates B-cells.

Often, due to the effects of a disease or even the treatments for a disease, a patient's immune response is diminished or the immune response is disadvantageously shifted away from a Th-1 pro-inflammatory type response and towards a Th-2 anti-inflammatory type response. This diminished or Th-2 polarized immune response is thought to be responsible, at least in part, for the more rapid progression of disease and reduction in the effectiveness of some treatments. This is thought to be true, for example, in cancer patients. In the context of other diseases, a heightened or Th-1 polarized immune response can be disadvantageous and at least partly responsible for the progression of the disease or reduction in the effectiveness of treatment. Thus, there is a need in the art for methods of modulating an immune response.

BRIEF SUMMARY OF THE INVENTION

The invention provides a method of enhancing an antigen-specific immune response in a host comprising administering to the host an HMGN polypeptide comprising HMGN1 (SEQ ID NO: 1), HMGN3a (SEQ ID NO: 2), HMGN3b (SEQ ID NO: 3), HMGN4 (SEQ ID NO: 4), Nsbp1(SEQ ID NO: 5), or a functional fragment thereof, in an amount effective to enhance an antigen-specific immune response.

In another aspect, the invention provides a method of enhancing the activation or recruitment of dendritic cells in a host comprising administering to the host an HMGN polypeptide comprising HMGN1 (SEQ ID NO: 1), HMGN3a (SEQ ID NO: 2), HMGN3b (SEQ ID NO: 3), HMGN4 (SEQ ID NO: 4), Nsbp1(SEQ ID NO: 5), or a functional fragment thereof, in an amount effective to enhance the activation or recruitment of dendritic cells in a host.

The invention also provides a method of shifting the Th-1/Th-2 balance of an immune response of a host towards a Th-1 type immune response comprising administering to the host an HMGN polypeptide comprising HMGN1 (SEQ ID NO: 1), HMGN3a (SEQ ID NO: 2), HMGN3b (SEQ ID NO: 3), HMGN4 (SEQ ID NO: 4), Nsbp1(SEQ ID NO: 5), or a functional fragment thereof, in an amount effective to shift the Th-1/Th-2 balance of an immune response of a host towards a Th-1 type immune response.

The invention further provides a pharmaceutical composition. According to one aspect of the invention, the pharmaceutical composition comprises (a) an HMGN polypeptide comprising HMGN1 (SEQ ID NO: 1), HMGN3a (SEQ ID NO: 2), HMGN3b (SEQ ID NO: 3), HMGN4 (SEQ ID NO: 4), Nsbp1(SEQ ID NO: 5), or a functional fragment thereof, and (b) an antigen, such as a tumor antigen. According to another aspect of the invention, the pharmaceutical composition comprises (a) a nucleic acid that encodes an HMGN polypeptide comprising HMGN1 (SEQ ID NO: 1), HMGN3a (SEQ ID NO: 2), HMGN3b (SEQ ID NO: 3), HMGN4 (SEQ ID NO: 4), Nsbp1(SEQ ID NO: 5), or a functional fragment thereof, and (b) a nucleic acid that encodes a tumor antigen.

In another aspect, the invention provides a method of suppressing an immune response in a host comprising administering to the host an HMGN polypeptide antagonist, wherein the HMGN polypeptide comprises HMGN1 (SEQ ID NO: 1), HMGN3a (SEQ ID NO: 2), HMGN3b (SEQ ID NO: 3), HMGN4 (SEQ ID NO: 4), or Nsbp1(SEQ ID NO: 5), in an amount effective to suppress the immune response.

BRIEF DESCRIPTION OF THE SEVERAL VIEWS OF THE DRAWINGS

FIG. 1A illustrates by way of several graphs the concentration of various cytokines (IL-6, IL-8, IL-12p70, and TNFα) in dendritic cell cultures treated with different concentrations of HMGN1 (SEQ ID NO: 1) or HMGN2. FIG. 1B illustrates by way of several graphs the concentration of various cytokines in control dendritic cell cultures (no treatment) and dendritic cell cultures treated with 1 µg/ml of HMGN1 (SEQ ID NO: 1) or HMGN2 as a function of time. In FIGS. 1A and 1B, data from control cultures is referenced by -○-, cultures treated with HMGN1 by -●-, and cultures treated with HMGN2 by -▲-.

FIG. 5 is a graph of the migration index of subpopulations of DC cells (CD11c+; CD11c+/CD11b+; CD11c+/B220+; and CD11c+/CD11b+/B220) in the peritoneal cavity of mice treated with HMGN1 (SEQ ID NO: 1) (black bars) and control mice treated only with phosphate buffer (PBS) (white bars).

FIG. 6A is a graph of cell proliferation (as represented by tritiated thymidine incorporation) plotted against ovalbumin (OVA) concentration in cultures of OVA-specific splenocytes harvested from mice treated with OVA alone (-○-) or OVA mixed with alum (-◆-) or HMGN1 (SEQ ID NO: 1) (-▲-). FIG. 6B presents graphs of the concentration of various cytokines in the same cultures.

FIG. 7A presents graphs of the concentration of various cytokines produced in response to in vitro stimulation with OVA by splenocytes from HMGN1 KO (HMGN1-/-) or wild-type (HMGN1+/+) mice immunized with OVA in the presence of alum. FIG. 7B presents graphs of the concentration of various cytokines produced in response to in vitro stimulation with OVA by splenocytes from HMGN1 KO (HMGN1-/-) or wild-type (HMGN1+/+) mice immunized with OVA in the presence of LPS.

FIGS. 9A and 9B are graphs of the amounts of various cytokines (pg/ml) produced by dendritic cells treated with 0, 0.1, or 1 μg/ml HMGN1 (SEQ ID NO: 1).

DETAILED DESCRIPTION OF THE INVENTION

Figure 2:
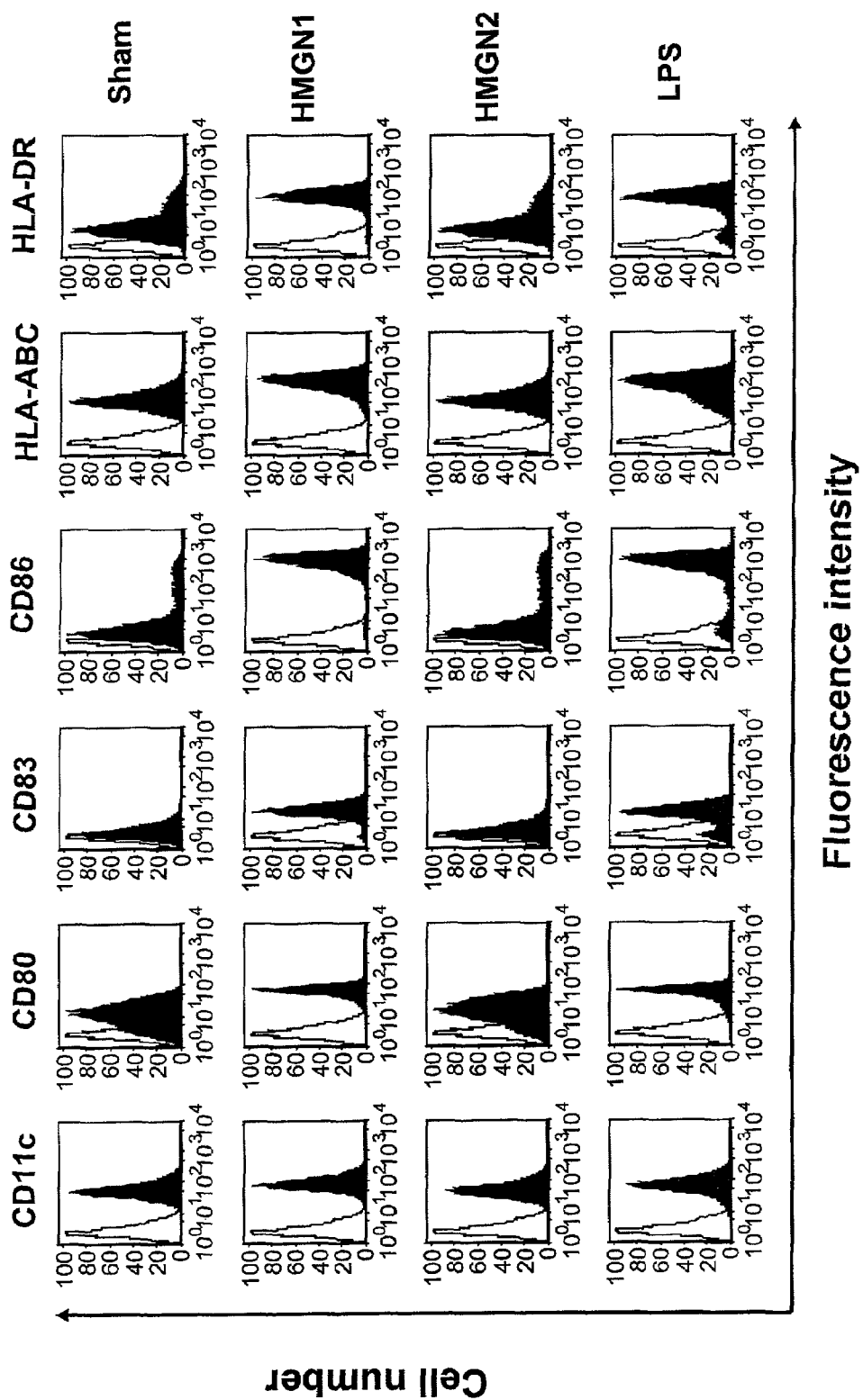
FIG. 2 presents flow cytometry histograms showing the proportion of cells (by number) expressing surface costimulatory molecules (CD80, CD83, and CD 86) and surface major histocompatibility complex (MHC) molecules (HLA-ABC and HLA-DR) in control dendritic cell cultures (no treatment or liposaccharide (LPS)-treated) and dendritic cell cultures treated with HMGN1 (SEQ ID NO: 1) or HMGN2. Surface expression of CD11c was measured as an additional control. Surface molecule expression is illustrated as a function of fluorescence intensity. The open-area curves represent staining with isotype-matched control antibody, and the shaded area curves represent staining with antibodies to the various surface molecules.

HMGN polypeptides are members of the high mobility group (HMG) family of chromosomal binding polypeptides. The HMG family is subdivided into three subfamilies, each of which has a characteristic functional sequence motif: HMGB (HMG-box motif), HMGN (nucleosomal binding domain), and HMGA (AT-hook motif). HMGN polypeptides include HMGN1 (formerly known as HMG14) (SEQ ID NO: 1), HMGN2, HMGN3a (SEQ ID NO: 2), HMGN3b (SEQ ID NO: 3), HMGN4 (SEQ ID NO: 4), and Nsbp1(NBD-45) (SEQ ID NO: 5).

It has been discovered that certain HMGN polypeptides can enhance an antigen-specific immune response. Thus, the invention provides methods of using HMGN polypeptides and functional fragments thereof to enhance an immune response in a host.

In one embodiment, the invention provides a method of enhancing an antigen-specific immune response in a host comprising administering to the host an HMGN polypeptide comprising HMGN1 (SEQ ID NO: 1), HMGN3a (SEQ ID NO: 2), HMGN3b (SEQ ID NO: 3), HMGN4 (SEQ ID NO: 4), Nsbp1(NBD-45) (SEQ ID NO: 5), or a functional fragment thereof (herein collectively referred to as "an HMGN polypeptide"), in an amount effective to enhance an antigen-specific immune response.

An antigen specific-immune response can be characterized by the production of lymphocytes that are capable of recognizing and differentiating the antigen from other antigens and mediating the destruction of the antigen. An antigen-specific immune response also can be characterized by the production, maturation, activation, or recruitment of antigen presenting cells.

An antigen-specific immune response is enhanced in accordance with the invention if the immune response to a given antigen is greater, quantitatively or qualitatively, after administration of an HMGN polypeptide as compared to the immune response in the absence of the administration of an HMGN polypeptide. A quantitative increase in an immune response encompasses an increase in the magnitude or degree of the response. The magnitude or degree of an immune response can be measured on the basis of any number of known parameters, such as an increase in the level of antigen-specific cytokine production (cytokine concentration), an increase in the number of lymphocytes activated (e.g., proliferation of antigen-specific lymphocytes) or recruited, and/or an increase in the production of antigen-specific antibodies (antibody concentration), etc. A qualitative increase in an immune response encompasses any change in the nature of the immune response that renders it more effective at combating a given antigen or disease. By way of illustration, an antigen-specific immune response typically includes two types of immune responses that occur simultaneously and exist in a relative balance: a Th-1 type response and a Th-2 type response. For the purposes of this invention, the quality of an immune response is considered enhanced in quality if the relative balance of the immune response is shifted towards the Th-1 type immune response and away from the Th-2 type immune response. Methods of distinguishing and measuring the relative balance of an immune response are known in the art. For example, measuring the types and levels of cytokines produced can distinguish and measure the relative balance of an immune response. A shift towards the Th-1 type response (e.g., after administration of an HMGN polypeptide) may be characterized by an increase in IFNγ and no increase or a reduced increase in IL-4, IL-5, and/or IL-13 (e.g., as compared to the levels of these cytokines before administration of an HMGN polypeptide). In other words, a shift towards a Th-1 type response can be characterized by an increase in the proportion of IFNγ relative to IL-4, IL-5, and/or IL-13. Conversely, a shift towards the Th-2 type response may be characterized by an increase in IL-4, IL-5, and/or IL-13 and no increase or a reduced increase in IFNγ (e.g., an increase in the proportion of IL-4, IL-5, and/or IL-13 relative to IFNγ). Another exemplary method may include measuring the subtypes of antigen-specific IgG antibodies produced during an immune response. A higher level (concentration) of IgG2a antibodies versus IgG1 antibodies suggests a Th1-type immune response. Conversely, a higher level (concentration) of IgG1 antibodies versus IgG2a antibodies suggests a Th2-type immune response. Qualitative and quantitative enhancements in an immune response can occur simultaneously, and are not mutually exclusive.

Preferably, the antigen-specific immune response is enhanced by shifting the Th-1/Th-2 balance of an immune response towards a Th-1 type response and away from a Th-2 type response, i.e., by enhancing or increasing the Th-1 type response or by decreasing or diminishing the Th-2 type response. Enhancing or increasing a Th1-type immune response may include increasing the production of cytokines such as IFNγ and/or TNFα and/or stimulating a cell-mediated immune response, such as the proliferation and activation of T-cells and/or macrophages specific for the antigen. Decreasing the Th2 immune response may include reducing the antibody-mediated, humoral immune responses and/or the production of interleukins 4, 5, and 13. In this respect, the invention also provides a method of shifting the Th-1/Th-2 balance of an immune response of a host towards a Th-1 type immune response, which method comprises administering to the host at least one HMGN polypeptide in an amount effective to shift the Th-1/Th-2 balance of an immune response of a host towards a Th-1 type immune response.

The antigen-specific immune response also can be enhanced by increasing or enhancing the activation or recruitment of dendritic cells. Thus, the invention provides, as a related aspect, a method of enhancing the activation or recruitment of dendritic cells in a host comprising administering to the host at least one HMGN polypeptide in an amount effective to enhance the activation or recruitment of dendritic cells in the host.

Activation of dendritic cells includes stimulating the maturation and/or the migration of dendritic cells to a specific locale (e.g., the site of an antigen or the site of chemotactic cytokine production, such as CCL2, CCL5, CCL19, CCL20, CCL21, etc.) and/or stimulating the maturation of dendritic cells. The activation of dendritic cells can be detected or measured by the production of cytokines associated with the activation of dendritic cells. In particular, the HMGN polypeptide (or a functional fragment thereof) may stimulate the dendritic cells to produce cytokines such as, for example, any or all of interleukin (IL)-6, IL-2, IL-8, IL-12, (e.g., IL-12p70), IL-1 (e.g., IL-1β), IL-10, IL-18, IL-23, tumor necrosis factors (TNF) (e.g., TNFα), and/or chemokines (e.g., keratinocyte chemoattractant (KC), CXCL8, CCL1, CCL2, CCL5, CCL7, CCL8, CCL13, CCL17, CCL18, CCL20, and/or CCL22). Activation of dendritic cells can also be detected or measured by the phosphorylation of mitogen-activated protein kinases (MAPKs) associated with the activation of dendritic cells. In particular, the HMGN polypeptide (or a functional fragment thereof) may stimulate the phosphorylation of MAPKs such as, for example, any or all of p44/42 MAPKs, p38 MAPKs, and/or c-Jun N-terminal kinase (JNK) MAPKs. In addition, the activation of dendritic cells can be detected or measured by the activation of nuclear factor kappa-light-chain-enhancer of activated B cells (NF-κB). In particular, the HMGN polypeptide (or a functional fragment thereof) may stimulate the activation of NF-κB and/or a decrease of I-κBα. Maturation of dendritic cells can be detected or measured on the basis of the expression of surface molecules that appear on mature dendritic cells. For example, mature dendritic cells typically express receptors that enable them to respond to chemokines produced by the lymph node (e.g., CCR7) and costimulatory (e.g., CD80, CD83, and CD86) and MHC (e.g., HLA-ABC and HLA-DR) molecules that assist in activating T-cells. Maturation of dendritic cells also can be detected by a cell shape having veils and elongated dendrites, increased motility toward chemokines (e.g., CCL19 and CCL21), or reduced capacity for endocytosis. Maturation of dendritic cells also can be detected indirectly by measuring the capacity of dendritic cells to stimulate the proliferation or differentiation of naive T-cells. Recruitment of dendritic cells can be measured or detected by the movement of dendritic cells to a given locale. Assays for measuring or detecting an increase in the activation and/or recruitment of dendritic cells are known in the art and described herein.

The HMGN polypeptides (including functional fragments thereof) can be obtained by methods known in the art. Suitable methods of de novo synthesizing polypeptides are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2000; and U.S. Pat. No. 5,449,752. Also, HMGN polypeptides (including functional fragments) and antigens can be recombinantly produced using the nucleic acids described herein and standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, the HMGN polypeptides (including functional fragments thereof) can be isolated and/or purified from a natural source, e.g., a human. Methods of isolation and purification are well-known in the art. In this respect, the HMGN polypeptides are exogenous and can be synthetic, recombinant, or of natural origin.

The functional fragment of the HMGN polypeptide can comprise any contiguous part of the HMGN polypeptide that retains a relevant biological activity of the HMGN polypeptide, e.g., enhances an antigen-specific immune response. Any given fragment of an HMGN polypeptide can be tested for such biological activity using methods described herein or otherwise known in the art. For example, the functional fragment can comprise, consist essentially of, or consist of the N-terminal nucleosomal binding domain (NBD) of the HMGN polypeptide (e.g., the sequence from $^{14}$Lys to $^{49}$Lys of HMGN1 (SEQ ID NO: 11), the sequence from $^{20}$Lys to $^{49}$Lys of HMGN3a/3b (SEQ ID NO: 12), the sequence from $^{18}$Lys to 47Lys of HMGN4 (SEQ ID NO: 13), and/or the sequence from $^{17}$Lys to $^{46}$Lys of Nsbp1(SEQ ID NO: 14)). In reference to the parent HMGN polypeptide, the functional fragment preferably comprises, for instance, about 10% or more, 25% or more, 30% or more, 50% or more, 60% or more, 80% or more, 90% or more, or even 95% or more of the parent HMGN polypeptide.

The HMGN polypeptides (including functional fragments) can be glycosylated, amidated, carboxylated, phosphorylated, esterified, N-acylated, cyclized via, e.g., a disulfide bridge, or converted into an acid addition salt and/or optionally dimerized or polymerized, or conjugated. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Of course, the method of the invention can comprise administering two or more HMGN polypeptides or functional fragment thereof, any of which may be the same or different from one another. Furthermore, the HMGN polypeptide or functional fragment thereof can be provided as part of a larger polypeptide construct. For instance, the HMGN polypeptide or functional fragment thereof can be provided as a fusion protein comprising an HMGN polypeptide or functional fragment along with other amino acid sequences or a nucleic acid encoding same. By way of further illustration, the HMGN polypeptide or functional fragment can be provided by two or more fragments of an HMGN polypeptide (e.g., two or more NBD domains, or at least one of each of the NBD domains), with or without a linking amino acid sequence and/or flanking sequences. The HMGN polypeptide or fragment thereof also can be provided as part of a conjugate or nucleic acid encoding same. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

The antigen can be any antigen against which an antigen-specific immune response is desired. In some embodiments, the antigen is a microbial antigen. The microbial antigen can be a bacterial (e.g., anthrax, tuberculosis, etc.) antigen or a viral (e.g., influenza, human immunodeficiency virus (HIV), etc.) antigen. Microbial antigens are molecules (e.g., polypeptide, lipid, carbohydrate, etc.) that are uniquely expressed by microbes, or greatly over-expressed by microbes as compared to non-microbes, such that an immune response to the antigen results in the more rapid destruction of the microbe as compared to non-microbes.

Preferably, the antigen-specific immune response is an immune response to a tumor antigen. Tumor antigens are molecules (e.g., polypeptide, lipid, carbohydrate, etc.) that are uniquely expressed by tumor cells, or greatly over-expressed by tumor cells as compared to non-tumor cells, such that an immune response to the antigen results in the more rapid destruction of tumor cells as compared to normal (non-cancerous) cells.

The tumor antigen can be an antigen expressed by any cell of any cancer or tumor. For example, the tumor antigen can be an antigen expressed by any cell of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, uterine cancer, esophageal cancer, cervical cancer, gastrointestinal carcinoid tumor, lymphoid and other hematopoietic tumors, Hodgkin lymphoma, B cell lymphoma, bronchial squamous cell cancer, hypopharynx cancer, kidney cancer, larynx cancer, liver cancer, pancreatic cancer, carcinoma, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

More specific examples of tumor antigens include polypeptides such as Ig-idiotype of B cell lymphoma, mutant cyclin-dependent kinase 4 of melanoma, Pmel-17 (gp100) of melanoma, MART-1 (Melan-A) of melanoma, p15 polypeptide of melanoma, tyrosinase of melanoma, MAGE 1, 2 and 3 of melanoma, thyroid medullary, small cell lung cancer, colon and/or bronchial squamous cell cancer, BAGE of bladder, melanoma, breast, and squamous-cell carcinoma, gp75 of melanoma, oncofetal antigen of melanoma; carbohydrate/lipids such as muci mucin of breast, pancreas, and ovarian cancer, GM2 and GD2 gangliosides of melanoma; oncogenes such as mutant p53 of carcinoma, mutant ras of colon cancer and HER21neu proto-onco-gene of breast carcinoma; viral products such as human papilloma virus polypeptides of squamous cell cancers of cervix and esophagus.

A method of the invention may further comprise administering an antigen to the host, especially a tumor antigen. The antigen can be any of those discussed above with respect to the antigen-specific immune response. Of course, two or more different antigens can be administered to the host.

When an antigen is administered in connection with a method of the invention, the antigen and HMGN polypeptide (or functional fragment thereof) can be administered simultaneously (as a single composition or in different compositions) or sequentially in any order. The methods may include administering the antigen first, followed by the HMGN polypeptide (or functional fragment thereof), or the method may include administering the HMGN polypeptide (or functional fragment thereof) first, followed by the antigen. Regardless of the order of the administration of the HMGN polypeptide (or functional fragment thereof) and the antigen, the HMGN polypeptide (or functional fragment thereof) and the antigen are preferably administered in close enough succession to enhance an immune response against the antigen.

The HMGN polypeptide (or functional fragment thereof) and the antigen also can be part of a fusion protein. The fusion protein can comprise one or more HMGN polypeptides (or functional fragments thereof) and/or one or more antigens. Suitable methods of making fusion proteins are known in the art, and include, for example, recombinant methods. See, for instance, Choi et al., *Mol. Biotechnol.* 31: 193-202 (2005). In other embodiments, the HMGN polypeptide, including any of the functional fragments thereof, may be provided as a conjugate with the antigen. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

The HMGN polypeptide or fragment thereof and the antigen, when used, can be administered to the host by administering a nucleic acid encoding such molecules to the host. "Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

Nucleic acids encoding the HMGN polypeptides and antigens discussed herein are known in the art (e.g., SEQ ID NOs: 6-10 and degenerate nucleic acid sequences encoding the same amino acid sequences), and can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides).

The nucleic acids can be incorporated into a recombinant expression vector. For purposes herein, the term "recombinant expression vector" means a genetically-modified oligonucleotide or polynucleotide construct that permits the expression of an mRNA or polypeptide by a host cell, when the construct comprises a nucleotide sequence encoding the mRNA or polypeptide, and the vector is contacted with the cell under conditions sufficient to have the mRNA or polypeptide expressed within the cell. The vectors are not naturally-occurring as a whole. However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages does not hinder the transcription or replication of the vector.

The recombinant expression vector can be any suitable recombinant expression vector, and can be used to transform or transfect any suitable host. Suitable vectors include those designed for propagation and expansion or for expression or both, such as plasmids and viruses. The vector can be of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2 µ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter and/or stop codon operably linked to the nucleotide sequence encoding the HMGN polypeptide (including functional fragments thereof), or to the nucleotide sequence which is complementary to the nucleotide sequence encoding the HMGN polypeptide or functional fragment thereof. The selection of stop codons and promoters, e.g., strong, weak, inducible, tissue-specific and developmental-specific, is within the ordinary skill of the artisan. Similarly, the combining of a nucleotide sequence with a stop codon and a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The HMGN polypeptides (including functional fragments thereof) and nucleic acids encoding such peptides can be of synthetic or natural origin, and can be isolated or purified to any degree. The terms "isolated" and "purified" as used herein means having been increased in purity, wherein "purity" is a relative term, and not to be necessarily construed as absolute purity. For example, the purity can be at least about 50%, can be greater than 60%, 70% or 80%, or can be 100%.

The methods described herein may be used for any purpose, e.g., the treatment or prevention of disease, especially cancer. Exemplary cancers that may be treated or prevented using the methods described herein may include any of those discussed above with respect to the tumor antigens.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof. With respect to the inventive methods, the cancer can be any cancer, including any of the cancers associated with any of the tumor antigens described herein.

For purposes of the invention, the amount or dose of the HMGN material administered should be sufficient to effect the desired biological response, e.g., a therapeutic or prophylactic response, in the subject or animal over a reasonable time frame. The dose will be determined by the efficacy of the particular HMGN material and the condition of the host (e.g., human), as well as the body weight of the host (e.g., human) to be treated. The dose of the HMGN material also will be determined by the existence, nature and extent of any adverse side effects that might accompany the administration of a particular HMGN material. Typically, the attending physician will decide the dosage of the HMGN material with which to treat each individual patient, taking into consideration a variety of factors, such as age, body weight, general health, diet, sex, HMGN material to be administered, route of administration, and the severity of the condition being treated.

The host referred to in the inventive methods can be any host capable of exhibiting an antigen-specific immune response. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. The host can be non-diseased, a host afflicted with a disease, such as cancer, or a host predisposed to a disease, such as cancer.

The invention also provides a pharmaceutical composition comprising (a) an HMGN polypeptide comprising HMGN1 (SEQ ID NO: 1), HMGN3a (SEQ ID NO: 2), HMGN3b (SEQ ID NO: 3), HMGN4 (SEQ ID NO: 4), Nsbp1(NBD-45) (SEQ ID NO: 5), or functional fragment thereof, and (b) an antigen, especially a tumor antigen. Alternatively, the pharmaceutical composition comprises (a) a nucleic acid encoding an HMGN polypeptide comprising HMGN1 (SEQ ID NO: 1), HMGN3a (SEQ ID NO: 2), HMGN3b (SEQ ID NO: 3), HMGN4 (SEQ ID NO: 4), Nsbp1(NBD-45) (SEQ ID NO: 5), or functional fragment thereof, and (b) a nucleic acid encoding an antigen, especially a tumor antigen. The pharmaceutical composition can, of course, comprise more than one HMGN polypeptide or fragment thereof (e.g., two or more different HMGN polypeptides) or one or more nucleic acids encoding more than one HMGN polypeptide or fragment thereof (e.g., two or more different HMGN polypeptides). Alternatively or in addition, the pharmaceutical composition can comprise more than one tumor antigen (e.g., two or more different antigens) or one or more nucleic acids encoding more than one tumor antigen (e.g., two or more different antigens). All other features of the HMGN polypeptides (including functional fragments thereof), antigens, tumor antigens, and nucleic acids are as described with respect to the methods of the invention.

The pharmaceutical composition can comprise other active ingredients in addition to the HMGN polypeptide, fragment thereof, and tumor antigen. For example, the pharmaceutical composition can comprise other pharmaceutically active agents or drugs, such as a chemotherapeutic agent, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.; biological response modifiers, e.g., bacillus calmette-guerin (BCG), etc.; cytokines, e.g., IL-2, IFNs, GM-CSF, etc.; and/or antibodies, e.g., trastuzumab (Herceptin®, available from Genentech, South San Francisco, Calif., U.S.A.), etc.

The pharmaceutical composition typically will comprise a carrier. Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use. The choice of carrier will be determined in part by the particular compounds used in the pharmaceutical composition, as well as by the particular method used to administer the HMGN material.

The following formulations for oral, intravenous, intramuscular, subcutaneous, or intraperitoneal administration are exemplary and are in no way limiting. More than one route can be used to administer the HMGN materials and/or tumor antigen, and in certain instances, a particular route can provide a more immediate and more effective response than another route.

Oral formulations may include any suitable carrier. For example, formulations suitable for oral administration may comprise suitable carriers, such as lactose, sucrose, starch, talc magnesium stearate, crystalline cellulose, methyl cellulose, carboxymethyl cellulose, glycerin, sodium alginate or gum arabic among others.

Intravenous, intramuscular, subcutaneous, or intraperitoneal formulations may include any suitable carrier. For example, formulations suitable for intravenous, intramuscular, subcutaneous, or intraperitoneal administration may comprise sterile aqueous solutions of the HMGN polypeptide (or functional fragment thereof) and/or the tumor antigen with solutions which are preferably isotonic with the blood of the recipient. Such formulations may be prepared by dissolving the HMGN polypeptide (or functional fragment thereof) and/or the tumor antigen in water containing physiologically compatible substances such as sodium chloride (e.g. 0.1-2.0M), glycine, and the like, and having a buffered pH compatible with physiological conditions to produce an aqueous solution, and rendering said solution sterile.

For purposes of the invention, the amount or concentration of the HMGN polypeptide or fragment thereof, tumor antigen, and other optional active ingredients used in the pharmaceutical composition should be sufficient to effect a desired biological response, e.g., a therapeutic or prophylactic response, in the subject or animal using a reasonable dosage regimen over a reasonable time frame. For example, the concentration of the HMGN polypeptide or fragment thereof, tumor antigen, and other optional active ingredients should be sufficient to enhance an antigen-specific immune response as defined herein with respect to the methods of the invention.

The pharmaceutical compositions of the invention may be used for any purpose, but are thought to be especially useful in conjunction with the methods of the invention and for the treatment or prevention of disease, such as cancer. Exemplary cancers that may be treated or prevented include acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, uterine cancer, esophageal cancer, cervical cancer, gastrointestinal carcinoid tumor, lymphoid and other hematopoietic tumors, Hodgkin lymphoma, B cell lymphoma, bronchial squamous cell cancer, hypopharynx cancer, kidney cancer, larynx cancer, liver cancer, pancreatic cancer, carcinoma, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

The pharmaceutical compositions of the invention may advantageously be nontoxic. Without being bound to any particular theory, it is believed that because the HMGN polypeptides are endogenous molecules, the administration of an HMGN polypeptide may not cause toxic effects in mammals, particularly, humans.

The invention also provides a method of suppressing an antigen-specific immune response in a host. The method comprises administering to the host an HMGN polypeptide antagonist, wherein the HMGN polypeptide comprises HMGN1 (SEQ ID NO: 1), HMGN3a (SEQ ID NO: 2), HMGN3b (SEQ ID NO: 3), HMGN4 (SEQ ID NO: 4), or Nsbp1(SEQ ID NO: 5), in an amount effective to suppress the immune response.

An immune response is suppressed in accordance with the invention if the immune response is diminished, quantitatively or qualitatively, after administration of an HMGN polypeptide antagonist as compared to the immune response in the absence of the administration of an HMGN polypeptide antagonist. A quantitative decrease in an immune response encompasses a decrease in the magnitude or degree of the response. The magnitude or degree of an immune response can be measured on the basis of any number of known parameters, such as a decrease in the level of cytokine (e.g., antigen-specific cytokine) production (cytokine concentration), a decrease in the number of lymphocytes activated (e.g., proliferation of lymphocytes (e.g., antigen-specific lymphocytes)) or recruited, and/or a decrease in the production of antibodies (antigen-specific antibodies) (antibody concentration), etc. A qualitative decrease in an immune response encompasses any change in the nature of the immune response that renders it less effective at mediating the destruction of a given antigen. For the purposes of this invention, the quality of an immune response is considered diminished if the relative balance of the immune response is shifted towards the Th-2 type immune response and away from the Th-1 type immune response. The relative balance of an immune response may be distinguished and measured by methods known in the art and as described herein. For example, a shift toward the Th-2 type response may be characterized by an increase in IL-4, IL-5, and/or IL-13 and no increase or a reduced increase in IFNγ. Conversely, a shift toward the Th-1 type response may be characterized by an increase in IFNγ and no increase or a reduced increase in IL-4, IL-5, and/or IL-13. Another exemplary method may include measuring the subtypes of antigen-specific IgG antibodies produced during an immune response. A lower level (concentration) of IgG2a antibodies versus IgG1 antibodies suggests a Th2-type immune response. Conversely, a lower level (concentration) of IgG1 antibodies versus IgG2a antibodies suggests a Th1-type immune response. Qualitative and quantitative diminishment of an immune response can occur simultaneously, and are not mutually exclusive.

Preferably, the immune response is suppressed by shifting the Th-1/Th-2 balance of an immune response towards a Th-2 type response and away from a Th-1 type response, i.e., by suppressing or decreasing the Th-1 type response or by increasing or enhancing the Th-2 type response. Suppressing or decreasing a Th1-type immune response may include decreasing the production of cytokines such as IFNγ and/or TNFγ and/or reducing a cell-mediated immune response, such as the proliferation and activation of T-cells and/or macrophages specific for the antigen. Decreasing the Th1 immune response may include increasing the antibody-mediated, humoral immune responses and/or the production of interleukins 4, 5, and 13.

The immune response also can be suppressed by decreasing or suppressing the activation or recruitment of dendritic cells. Suppressing the activation of dendritic cells includes reducing the maturation and/or the migration of dendritic cells, e.g., to a specific locale (e.g., the site of an antigen or the site of chemotactic cytokine production, such as CCL2, CCL5, CCL19, CCL20, CCL21, etc.). Suppressing the activation of dendritic cells can be measured by the lack of production of cytokines associated with the activation of dendritic cells. In particular, the HMGN polypeptide antagonist may suppress the dendritic cell production of cytokines such as, for example, any or all of interleukin (IL)-6, IL-8, IL-12, (e.g., IL-12p70), IL-1 (e.g., IL-1β), IL-10, IL-18, IL-23, tumor necrosis factors (TNF) (e.g., TNFα), and/or chemokines (e.g., CXCL8, CCL1, CCL2, CCL5, CCL7, CCL8, CCL13, CCL17, CCL18, CCL20, and/or CCL22). The lack of mature dendritic cells, or a reduction in mature dendritic cells, can be detected or measured on the basis of the lack of expression of surface molecules that appear on mature dendritic cells. For example, immature dendritic cells typically do not express receptors that enable them to respond to chemokines produced by the lymph node (e.g., CCR7) or costimulatory (e.g., CD80, CD83, and CD86) or MHC (e.g., HLA-ABC and HLA-DR) molecules that assist in activating T-cells. Immature dendritic cells also can be detected by a cell shape lacking veils and elongated dendrites, decreased motility toward chemokines (e.g., CCL19 and CCL21), or increased capacity for endocytosis. Immature dendritic cells can also be detected indirectly by measuring the inability of dendritic cells to stimulate the proliferation or differentiation of naive T-cells. The absence of recruitment of dendritic cells can be measured or detected by a lack of movement of dendritic cells to a given locale. Assays for measuring or detecting a decrease in the activation and/or recruitment of dendritic cells are known in the art and described herein.

The HMGN antagonist can be any agent that inhibits the biological activity of an HMGN polypeptide. Inhibition of an HMGN polypeptide may be characterized by suppression of an immune response in any of the ways described herein. The HMGN antagonists include agents that bind to the HMGN polypeptide or functional fragment thereof (e.g., the NBD of the HMGN polypeptide), thereby inhibiting its function, as well as agents that compete with the HMGN polypeptide or functional fragment thereof (e.g., the NBD of the HMGN polypeptide) for the native HMGN binding site. By way of illustration, the HMGN antagonist can be an antibody or antibody fragment, an antisense nucleotide, or a chemical inhibitor (e.g., small molecule or peptide inhibitor).

Anti-HMGN antibodies and antibody fragments can be monoclonal or polyclonal. Anti-HMGN antibodies and antibody fragments can be prepared using the HMGN proteins disclosed herein and routine techniques. Examples of such antibodies or antibody fragments include those specific to a functional domain of HMGN (e.g., nucleosomal binding domain).

Antisense nucleic acid (e.g., RNA or DNA) include, for example, interfering nucleic acids such as RNAi and siRNA molecules. Such antisense nucleic acids are commercially available and can be prepared using the nucleic acid sequences encoding the HMGN polypeptides disclosed herein and routine techniques.

Chemical inhibitors of HMGN include small molecules and peptides that bind the HMGN polypeptide or functional fragment thereof or compete with the HMGN polypeptide or functional fragment thereof for its native binding site. Suitable inhibitors can include, for example, a non-active fragment or mutant of an HMGN polypeptide. Chemical inhibitors of HMGN can be identified using routine techniques. For example, chemical inhibitors can be tested in binding assays to identify molecules and peptides that bind to a given HMGN polypeptide or functional fragment thereof with sufficient affinity to inhibit HMGN biological function. Also, competition assays can be performed to identify small-molecules and peptides that compete with HMGN or functional fragment thereof for binding to its native binding site. Such techniques could be used in conjunction with mutagenesis of the HMGN polypeptide or functional fragment thereof itself, and/or with high-throughput screens of known chemical inhibitors.

The methods of suppressing an immune response described herein may be used for any purpose, e.g., the treatment or prevention of a disease associated with a heightened or Th-1 polarized immune response, particularly any disease that may be effectively treated or prevented by shifting the Th-1/Th-2 balance of an immune response away from a Th1-type response and toward a Th2-type response. Exemplary diseases that may be treated or prevented using the methods of suppressing an immune response described herein include parasitic infections (e.g., *Giardia intestinalis, Trichomonas vaginalis, Cryptosporidium, Toxoplasma gondii* and *Leishmania major*) and inflammatory or autoimmune disorders (e.g., atherosclerosis; asthma; lung fibrosis; bronchitis; respiratory distress syndrome; obstructive pulmonary disease; allergies; multiple sclerosis; dermatitis; psoriasis; gastroenteritis; colitis (e.g., ulcerative colitis); Crohn's disease; cystic fibrosis; celiac disease; inflammatory bowel disease; conjunctivitis; uveitis; autoimmune kidney disease; diabetic nephropathy; cachexia; coronary restenosis; sinusitis, cystitis; urethritis; serositis; uremic pericarditis; cholecystis; vaginitis; drug reactions; hepatitis; pelvic inflammatory disease; multiple myeloma; vitiligo; alopecia; Addison's disease; Hashimoto's disease; Graves disease; atrophic gastritis/pernicious anemia; acquired hypogonadism/infertility; hypoparathyroidism; multiple sclerosis; Myasthenia gravis; Coombs positive hemolytic anemia; systemic lupus erthymatosis; Siogren's syndrome, rheumatoid arthritis; endotoxemia; and immune mediated (type-1) diabetes).

For purposes of the invention, the amount or dose of the HMGN polypeptide antagonist administered should be sufficient to effect the desired biological response, e.g., a therapeutic or prophylactic response, in the subject or animal over a reasonable time frame. The dose will be determined by the efficacy of the particular HMGN polypeptide antagonist and the condition of the host (e.g., human), as well as the body weight of the host (e.g., human) to be treated. The dose of the HMGN polypeptide antagonist also will be determined by the existence, nature and extent of any adverse side effects that might accompany the administration of a particular HMGN polypeptide antagonist. Typically, the attending physician will decide the dosage of the HMGN polypeptide antagonist with which to treat each individual patient, taking into consideration a variety of factors, such as age, body weight, general health, diet, sex, HMGN polypeptide antagonist to be administered, route of administration, and the severity of the condition being treated.

Carriers, formulations, and routes of administration of the HMGN polypeptide antagonist may be any of those described herein for the administration of the HMGN polypeptide.

The following examples further illustrate the invention but, of course, should not be construed as in any way limiting its scope.

EXAMPLE 1

This example demonstrates that HMGN1 (SEQ ID NO: 1) induces dendritic cells to produce cytokines in a dose-dependent manner.

Human dendritic cells were cultured for 24 hours in RPMI 1640 medium, which contains 10% fetal bovine serum, 50 ng/mL recombinant human (rh) GM-CSF, 50 ng/mL rhIL-4. The cultures were treated with either HMGN1 (SEQ ID NO: 1) or HMGN2 at concentrations of 0, 0.2, 1, or 5 µg/mL. Untreated culture (sham) served as a control. The supernatants of the dendritic cell cultures were assayed for IL-6, IL-8, IL-12p70, and TNFα concentration by cytokine array. Experiments were repeated three times and the average (mean±SD) determined. The results are presented in FIG. 1A.

As shown in FIG. 1A, HMGN1 (SEQ ID NO: 1) stimulated the production of IL-6, IL-8, IL-12p70, and TNFα in dendritic cells a dose-dependent manner, whereas HMGN2 and untreated cultures showed no significant production of these cytokines. These results support the use of HMGN1 (SEQ ID NO: 1) to activate and/or recruit dendritic cells and enhance an immune response.

EXAMPLE 2

This example demonstrates that HMGN1 (SEQ ID NO: 1) induces dendritic cells to produce cytokines in a time-dependent manner.

Human dendritic cells were cultured for 24 hours in RPMI 1640 medium. The cultures were treated with 1 µg/mL of HMGN1 (SEQ ID NO: 1) or HMGN2, and the supernatents were analyzed by cytokine array for IL-6, IL-8, IL-12p70, and TNFα concentration at 6, 24, and 48 hours. Untreated culture (sham) served as a control. Experiments were repeated three times and the average (mean±SD) determined. The results are presented in FIG. 1B.

As shown in FIG. 1B, HMGN1 (SEQ ID NO: 1) stimulates the production of IL-6, IL-8, IL-12p70, and TNFα in a time-dependent manner, whereas HMGN2 and untreated cultures showed no significant production of these cytokines. These results support the use of HMGN1 (SEQ ID NO: 1) to activate and/or recruit dendritic cells and enhance an immune response.

EXAMPLE 3

This example demonstrates that HMGN1 (SEQ ID NO: 1) upregulates dendritic cell expression of surface costimulatory molecules and surface MHC molecules.

Human dendritic cells were cultured for 48 hours at 37° C. in a $CO_2$ incubator in RPMI 1640 medium. Cultures were treated with 1 µg/mL of HMGN1 (SEQ ID NO: 1) or HMGN2. Culture treated with 1 µg/mL lipopolysaccharide (LPS) and untreated culture (sham) served as positive and negative controls, respectively. The dendritic cells were immunostained and analyzed for the expression of surface molecules by flow cytometry. The results are presented in FIG. 2, wherein open-area curves represent staining with isotype-matched control antibody, and shaded-area curves represent staining with antibodies against the various surface molecules.

As shown in FIG. 2, treatment with HMGN1 (SEQ ID NO: 1) induces significantly greater expression of costimulatory molecules (CD80, CD83, and CD 86) and MHC molecules (HLA-ABC and HLA-DR) as compared to treatment with HMGN2 or without treatment. These results support the use of HMGN1 (SEQ ID NO: 1) to activate dendritic cells and enhance an immune response.

EXAMPLE 4

This example demonstrates that HMGN1 (SEQ ID NO: 1) enhances the antigen-presenting capacity of human dendritic cells.

Human dendritic cells were cultured with RPMI 1640 medium for 48 hours. Cultures were treated with either HMGN1 (SEQ ID NO: 1) (1 µg/mL) or HMGN2 (1 µg/mL). Culture treated with LPS (1 µg/mL) (as a positive control) and untreated culture (sham) served as positive and negative controls, respectively. The cultured cells were then used to stimulate the proliferation of allogeneic human T cells ($10^5$) in a mixed lymphocyte reaction. The proliferation of allogeneic T cells was measured as a function of tritiated thymidine ($^3$H-TdR) incorporation. The results are presented in FIG. 3.

Figure 3:
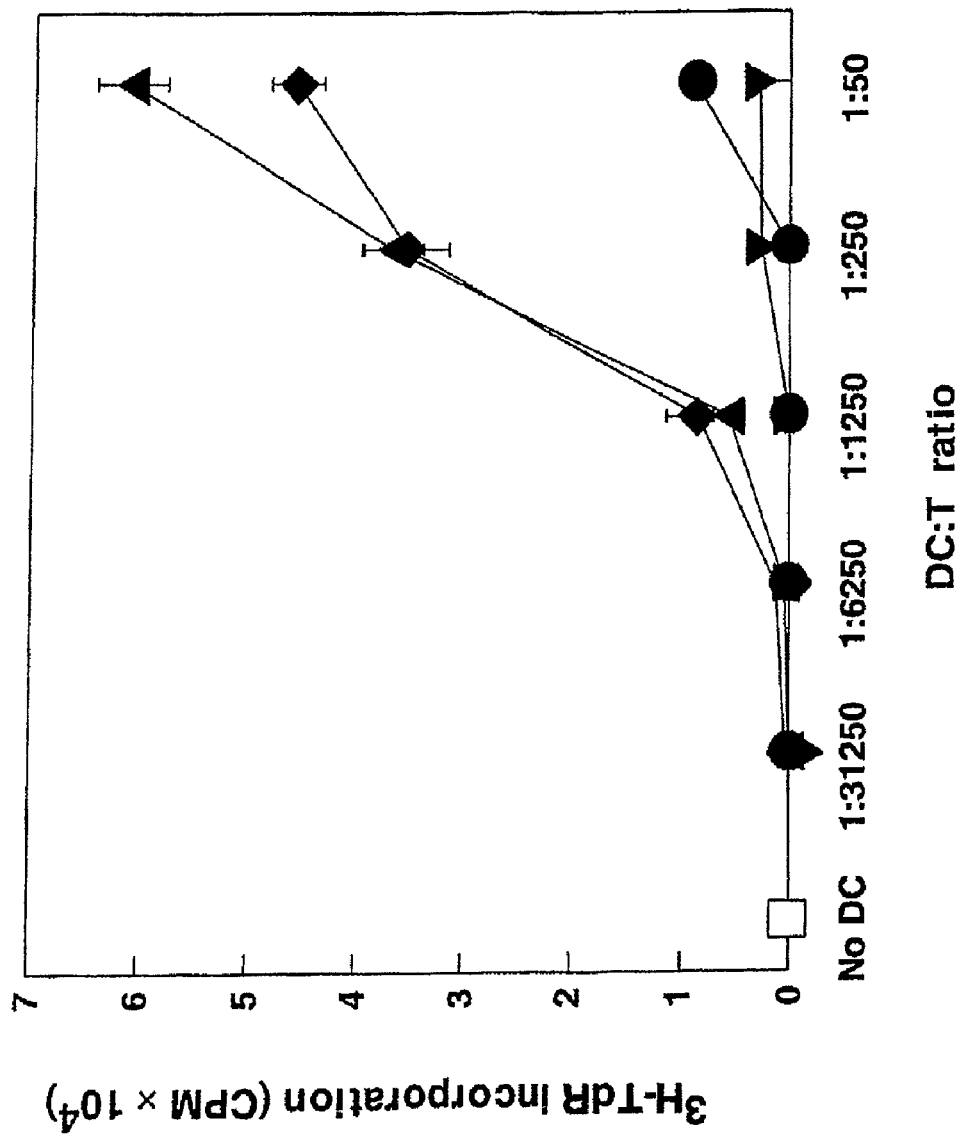
FIG. 3 is a graph of T-cell proliferation (as represented by tritiated thymidine incorporation) plotted against the ratio of dendritic cells to T-cells (DC:T) in dendritic cell/mixed lymphocyte reaction cultures. Treated cultures contained dendritic cells (DCs) exposed to 1 µg/ml HMGN1 (SEQ ID NO: 1) (-▲-), HMGN2 (-▼-), or LPS (-◆-). Untreated culture (contained sham-treated DCs (-●-)) and mixed lymphocyte reaction culture without dendritic cells (-□-) served as controls.

As shown in FIG. 3, dendritic cells treated with HGMN1 stimulated the proliferation of allogeneic T cells to a degree equal to or greater than that demonstrated by the positive control. HMGN2-treated culture and the negative control showed no significant amount of T-cell proliferation. These results support the use of HMGN1 (SEQ ID NO: 1) to activate dendritic cells and enhance an immune response.

EXAMPLE 5

This example demonstrates that HMGN1 (SEQ ID NO: 1) stimulates the maturation of dendritic cells.

Human dendritic cells were cultured with RPMI 1640 medium for 48 hours. Cultures were treated with either HMGN1 (SEQ ID NO: 1) (1 µg/mL) or HMGN2 (1 µg/mL).

Culture treated with LPS (1 µg/mL) (as a positive control) and untreated culture (sham) served as positive and negative controls, respectively. The migratory response of the dendritic cells toward CCL5, CCL21, and CXCL12 chemokines was measured according to the number of cells per high power field (No./HPF). The average number of dendritic cells (mean±SD of triplicate wells) that migrated in response to the chemokines is presented in FIG. 4.

Figure 4:
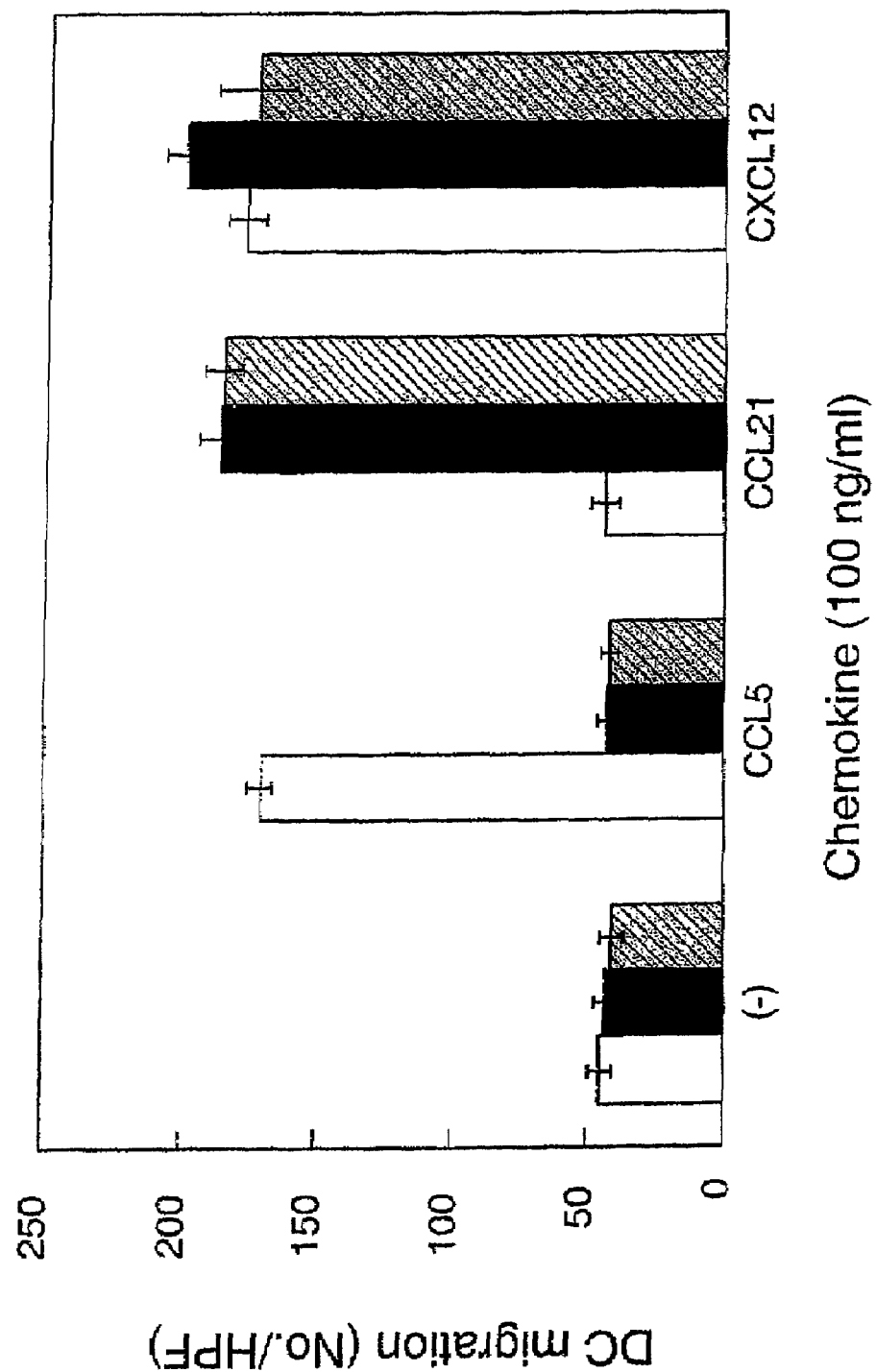
FIG. 4 is a graph of dendritic cell migration (number of cells per high power field (No./HPF)) towards various cytokines (CCL5, CCL21, and CXCL12) in cultures treated with 1 µg/ml HMGN1 (SEQ ID NO: 1) (diagonal striped bars) or LPS (black bars), and in untreated culture (contained sham-treated DCs (white bars)). Cell migration without any cytokine was measured as an additional control.

As shown in FIG. 4, dendritic cells in the negative control culture (sham) migrated toward CCL5 and not CCL21, indicating immaturity. Conversely, dendritic cells cultured in the presence of HMGN1 (SEQ ID NO: 1) migrated toward CCL21 and not CCL5. These results indicate that HMGN1 (SEQ ID NO: 1) treatment converted the dendritic cells from CCL5-responsive to CCL21-responsive, which is characteristic of dendritic cell maturation. The results support the use of HMGN1 (SEQ ID NO: 1) to activate dendritic cells and enhance an immune response.

EXAMPLE 6

This example demonstrates that HMGN1 (SEQ ID NO: 1) stimulates the recruitment of dendritic cells.

C57BL/6 mice (female, 3/group, 10 weeks old) were injected intraperitoneally with PBS alone (control) or PBS containing 1 µg of HMGN1 (SEQ ID NO: 1). After 4 hours, the cells in the peritoneal cavity were washed out, stained with antibodies against surface markers characteristic of mouse dendritic cells (CD11c+, CD11c+/CD11b+, CD11c+/B220+, CD11c+/CD11b+/B220+), and analyzed by flow cytometery. The results are presented in FIG. 5.

As shown in FIG. 5, HMGN1 (SEQ ID NO: 1) treatment stimulated the accumulation of various subpopulations of mouse dendritic cells (CD11c+, CD11c+/CD11b+, CD11c+/B220+, CD11c+/CD11b+/B220+) into the peritoneal cavity. These results support the use of HMGN1 (SEQ ID NO: 1) to recruit dendritic cells and enhance an immune response in vivo.

EXAMPLE 7

This example demonstrates that HMGN1 (SEQ ID NO: 1) promotes an antigen-specific immune response.

C57BL/6 mice (female, 4/group, 8 weeks old) were intraperitoneally immunized with ovalbumin (OVA) alone, OVA mixed with alum (2.5 mg), or HMGN1 (SEQ ID NO: 1) (1µg) on Day 1, booster immunized with OVA alone on Day 14, and euthanized on Day 21. The splenocytes of immunized mice were stimulated in vitro with OVA (0, 2, 10, and 50 µg/ml) for 5 days to measure OVA-specific proliferation (FIG. 6A) or stimulated with 20 µg/mL of OVA for 3 days (FIG. 6B). Cytokine production was measured, and the results are presented in FIGS. 6A and 6B.

As shown in FIG. 6A, the splenocytes of mice immunized with OVA plus HMGN1 (SEQ ID NO: 1) proliferated vigorously in a dose dependent manner upon in vitro OVA stimulation, indicating that HMGN1 (SEQ ID NO: 1) promoted an OVA-specific immune response. As shown in FIG. 6B, the splenocytes of mice immunized with OVA plus HMGN1 (SEQ ID NO: 1) produced significant amounts of IFNγ and TNFα, but not IL-4, indicating that HMGN1 (SEQ ID NO: 1) predominantly enhanced a Th1-type immune response. Conversely, alum, which served as a control that predominantly enhances a Th2 immune response, produced a high level of IL-4 and did not increase IFNγ. These results support the use of HMGN1 (SEQ ID NO: 1) to enhance an antigen-specific immune response and to shift the Th-1/Th-2 balance of an immune response of a host towards a Th-1 type immune response.

EXAMPLE 8

This example demonstrates the importance of HMGN1 (SEQ ID NO: 1) to the antigen-specific immune response in vivo.

HMGN1 knockout (HMGN1−/−) and littermate-matched WT (HMGN1+/+) mice (4 mice/group) were intra-peritoneally immunized on day 1 with ovalbumin (OVA) in the presence of alum or LPS, and boosted on day 14. On day 21, spleens of each group of immunized mice were pooled for the preparation of single splenocyte suspension. Subsequently, the splenocytes were stimulated in vitro with OVA for 48 hours and the cytokine concentrations in the supernatants were measured by cytokine array.

As shown in FIGS. 7A and 7B, splenocytes from HMGN1 knockout mice produced significantly less T cell cytokines (e.g., IL-4, IL-13, and IFNγ) as compared to wild-type mice, irrespective of adjuvant used (alum or LPS). These results show that HMGN1 (SEQ ID NO: 1) plays a significant role in the generation of a T-cell immune response.

EXAMPLE 9

This example demonstrates that the administration of exogenous HMGN1 (SEQ ID NO: 1) promotes an antigen-specific immune response in vivo.

C57BL/6 mice (4/group) were immunized with anthrax vaccine adsorbed (AVA) alone or in combination with 1~5 µg/mouse of HMGN1 (SEQ ID NO: 1) on day 1 and day 14 (boost). On day 10 and day 21, serum samples were taken from all mice and anti-AVA specific antibody titers were measured by ELISA.

Figures 8A, 8B:
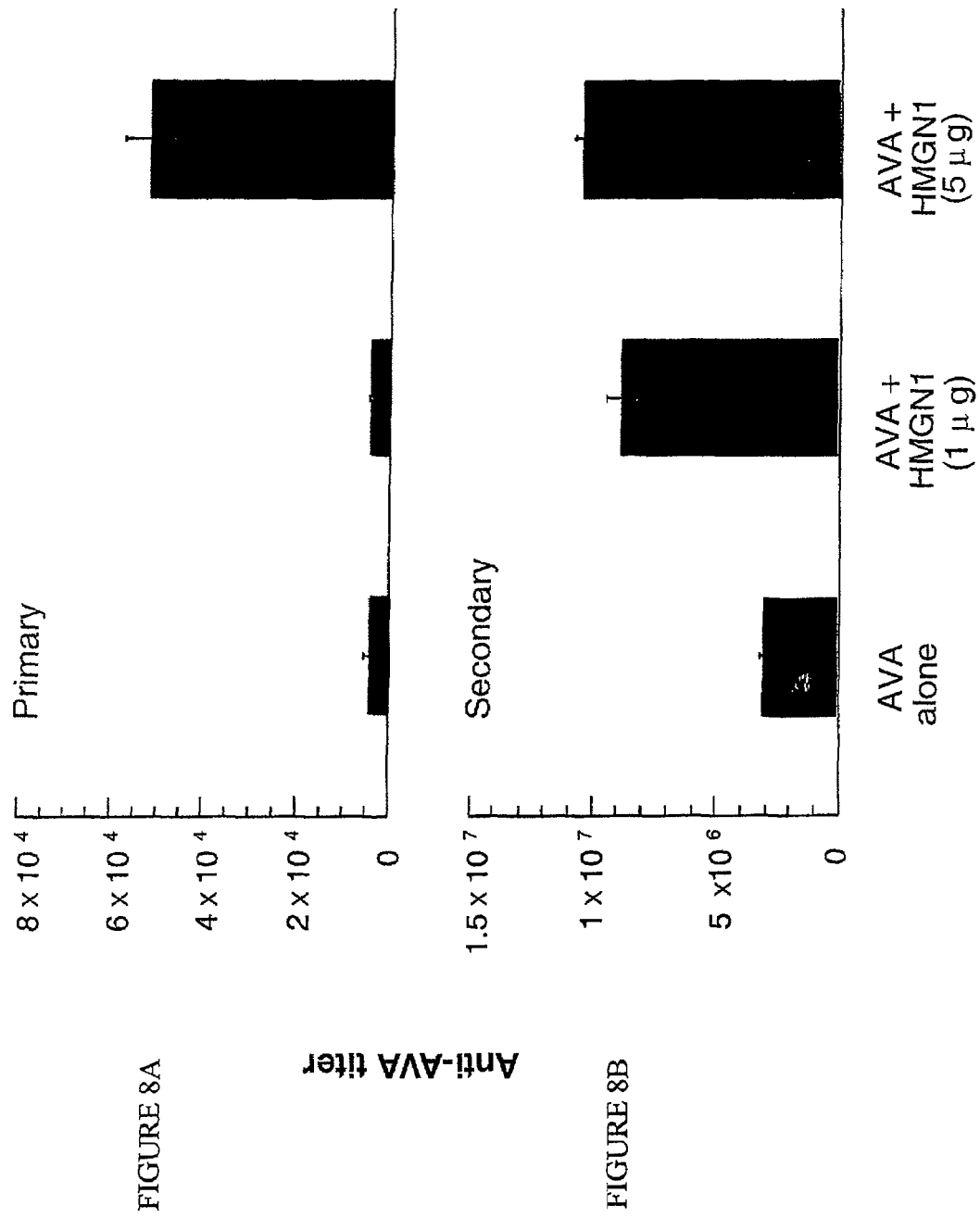
FIG. 8A is a graph of the number of primary anti-anthrax vaccine adsorbed (AVA) antibodies produced in mice immunized with AVA alone or in the presence of 1 μg or 5 μg of HMGN1 (SEQ ID NO: 1).
FIG. 8B is a graph of the number of secondary anti-AVA antibodies produced in mice immunized with AVA alone or in the presence of 1 μg or 5 μg of HMGN1 (SEQ ID NO: 1).

As shown in FIGS. 8A and 8B, mice immunized with AVA+HMGN1 (SEQ ID NO: 1) (1 µg/mouse) produced a higher level of secondary (day 21) anti-AVA antibodies as compared to mice immunized with AVA only. HMGN1 (SEQ ID NO: 1) at 5 µg/mouse (5~10 fold) enhanced both primary (day 10) and secondary (day 21) anti-AVA antibody responses. These results support the use of HMGN1 (SEQ ID NO: 1) to enhance an antigen-specific immune response.

EXAMPLE 10

This example demonstrates that HMGN1 (SEQ ID NO: 1) induces dendritic cells to produce cytokines.

Mice bone marrow-derived DCs were treated with various doses of HMGN1 (SEQ ID NO: 1) for 24 hours and the production of various inflammatory cytokines in the supernatants were subsequently measured by cytokine array.

As shown in FIGS. 9A and 9B, HMGN1 (SEQ ID NO: 1) stimulated the production of various inflammatory cytokines (TNFα, IL-1β, keratinocyte chemoattractant (KC), IL-10, IL-6, and IL-12p70) by mouse DCs. The results support the use of HMGN1 (SEQ ID NO: 1) to activate and/or recruit dendritic cells and modulate an immune response.

EXAMPLE 11

This example demonstrates to importance of HMGN1 (SEQ ID NO: 1) to the inflammatory immune response in vivo.

HMGN1 WT (HMGN1+/+) or KO (HMGN1−/−) mice (4 mice/group) were immunized intraperitoneally with OVA alone or OVA in the presence of alum or LPS (endotoxin). At 24 or 96 hours after the immunization, mouse serum samples were taken and various cytokines were measured.

Figure 10A:
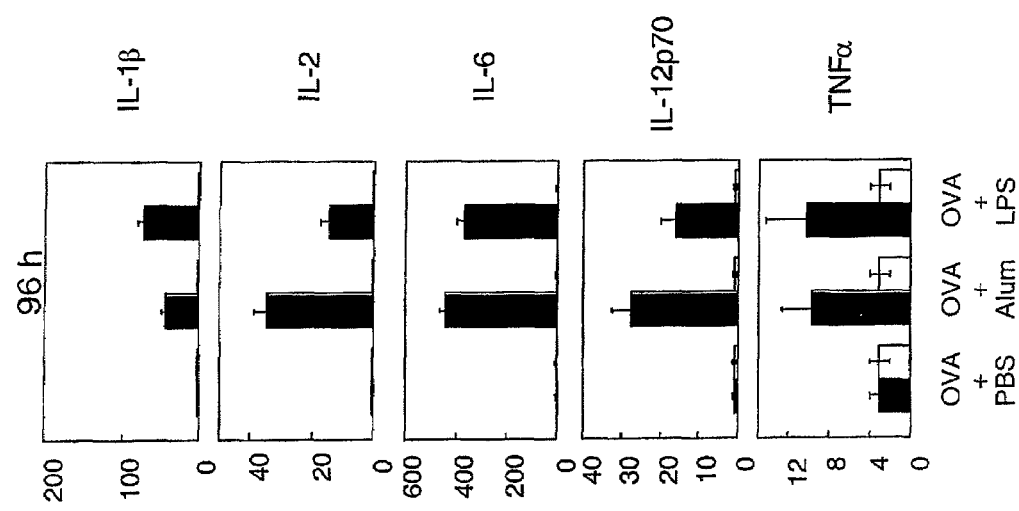
FIG. 10A is a graph of the concentration of various cytokines produced by HMGN1 KO (HMGN1-/-) (white bars) or wild-type (HMGN1+/+) (black bars) mice 24 hours after injection with OVA alone or OVA in the presence of alum or LPS.
Figure 10B:
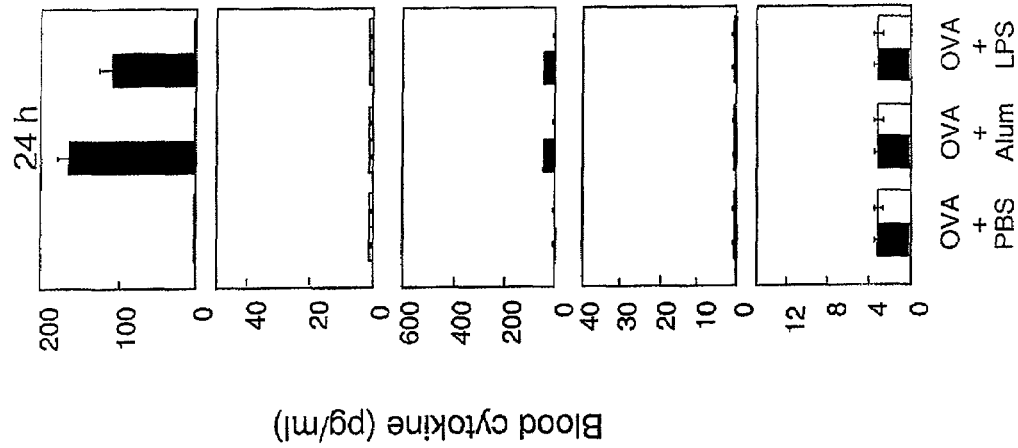
FIG. 10B is a graph of the concentration of various cytokines produced by HMGN1 KO (HMGN1-/-) (white bars) or wild-type (HMGN1+/+) (black bars) mice 96 hours after injection with OVA alone or OVA in the presence of alum or LPS.

As shown in FIG. 10A, HMGN1 KO mice failed to produce detectable levels of the inflammatory cytokines tested (IL-1β, IL-2, IL-6, and IL-12p70) at 24 and 96 hours after immunization, and produced less TNFα at 96 hours as compared to HMGN1 WT mice, irrespective of the adjuvant used for the immunization (either alum or LPS). These results demonstrate the importance of HMGN1 (SEQ ID NO: 1) in the induction of inflammatory cytokines, and support the use of HMGN1 (SEQ ID NO: 1) as a basis to modulate the inflammatory response, such as through the use of HMGN1 (SEQ ID NO: 1) inhibitory molecules.

EXAMPLE 12

This example demonstrates that HMGN1 (SEQ ID NO: 1) stimulates the activation of dendritic cells.

Mouse bone marrow-derived DCs were untreated or treated with HMGN1 (SEQ ID NO: 1) (at 1 μg/ml) at 37° C. for 20 or 60 minutes. At the end of treatment, DCs were washed extensively with ice-cold PBS, pelleted, and solubilized in sodium dodecyl sulfate polyacrylamide gel electrophoresis (SDS-PAGE) lysis buffer (at $10^7$/ml) to make cell lysate. DC lysates were then loaded onto SDS-PAGE gels, separated by electrophoresis, and transferred onto pieces of polyvinylidene fluoride (PVDF) membrane.

The PVDF membranes were analyzed by Western blot. Briefly, the membranes were washed, blocked, and reacted with rabbit anti-I-κBα, anti-phosphorylated p44/42 mitogen-activated protein kinases (MAPKs), anti-phosphorylated p38 MAPK, or anti-phosphorylated c-Jun N-terminal kinase (JNK) MAPK antibodies in a cold room overnight. After removal of unbound antibodies by washes, the PVDF membranes were reacted with horseradish peroxidase (HRP)-conjugated anti-rabbit IgG antibody, washed, developed with an Amersham enhanced luminol-based chemiluminescent (ECL™) kit, and autoradiographed. The PVDF membranes were then stripped and re-probed with anti-glyceraldehyde-3-phosphate dehydrogenase (GAPDH), anti-p44/42, anti-p38, and anti-JNK antibodies, respectively.

Figure 11:
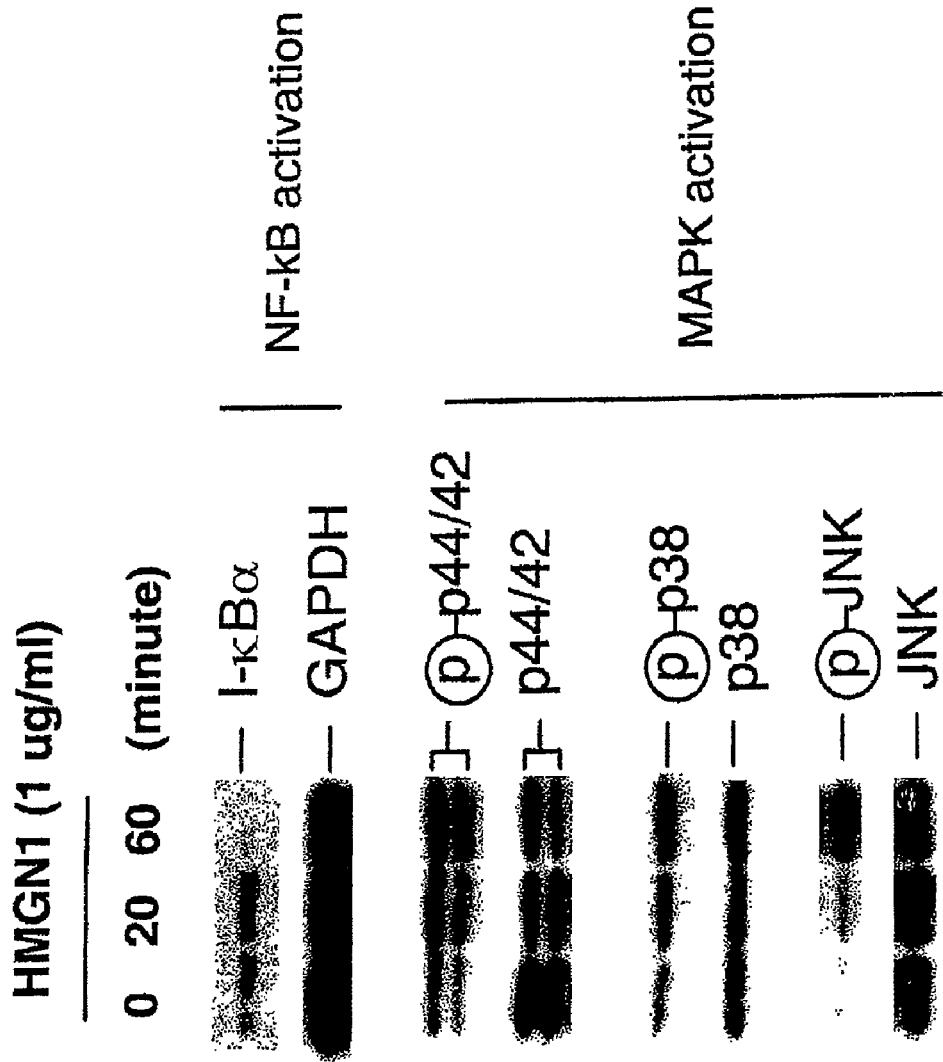
FIG. 11 presents a Western blot of untreated or HMGN1 (SEQ ID NO: 1)-treated (20 or 60 minutes) DC lysates probed with anti-I-κBα, anti-glyceraldehyde-3-phosphate dehydrogenase (GAPDH), anti-phosphorylated p44/42 mitogen-activated protein kinases (MAPKs), anti-p44/42 MAPKs, anti-phosphorylated p38 MAPK, anti-p38 MAPK, anti-phosphorylated c-Jun N-terminal kinase (JNK) MAPK, or anti-JNK MAPK antibodies.

The results are summarized in FIG. 11. As shown in FIG. 11, HMGN1 (SEQ ID NO: 1) treatment of mouse DCs decreased the level of I-κBα by the 60 minute time point, indicating the activation of nuclear factor kappa-light-chain-enhancer of activated B cells (NF-κB) in DCs. Similar band intensity for the three lanes confirms that a similar amount of total DC lysate proteins was loaded into each lane.

For the MAPKs, HMGN1 (SEQ ID NO: 1) treatment caused phosphorylation of three classes of MAPKs in a time-dependent manner (as evidenced by the intensified bands of phosphorylated p44/42, phosphorylated p38, and phosphorylated JNK), indicating the activation of three classes of MAPKs. The bands of p44/42, p38, and JNK were similar between 0, 20, and 60 minute time points, indicating that HMGN1 (SEQ ID NO: 1) treatment did not change the level of unactivated MAPKs.

These results support the use of HMGN1 (SEQ ID NO: 1) to activate dendritic cells and enhance an immune response.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of enhancing an antigen-specific immune response in a host comprising administering to the host an antigen and a polypeptide comprising HMGN1 (SEQ ID NO: 1) in an amount effective to enhance an antigen-specific immune response, wherein the method further comprises administering to the host one or more of HMGN3a (SEQ ID NO: 2), HMGN3b (SEQ ID NO: 3) HMGN4 (SEQ ID NO: 4), and Nsbp1 (SEQ ID NO: 5).

2. A method of enhancing the activation or recruitment of dendritic cells in a host comprising administering to the host an antigen and a polypeptide comprising HMGN1 (SEQ ID NO: 1) in an amount effective to enhance the activation or recruitment of dendritic cells in the host, wherein the method further comprises administering to the host one or more of HMGN3a (SEQ ID NO: 2), HMGN3b (SEQ ID NO: 3), HMGN4 (SEQ ID NO: 4), and Nsbp1 (SEQ ID NO: 5).

3. A method of shifting the Th-1/Th-2 balance of an immune response of a host towards a Th-1 type immune response comprising administering to the host an antigen and a polypeptide comprising HMGN1 (SEQ ID NO: 1) in an amount effective to shift the Th-1/Th-2 balance of an immune response towards a Th-1 type immune response, wherein the method further comprises administering to the host one or more of HMGN3a (SEQ ID NO: 2), HMGN3b (SEQ ID NO: 3), HMGN4 (SEQ ID NO: 4), and Nsbp1 (SEQ ID NO: 5).

4. The method of claim 1, wherein the method comprises administering two or more different antigens to the host.

5. The method of claim 1, wherein the antigen is a tumor antigen or microbial antigen.

6. The method of claim 5, wherein the tumor antigen is a melanoma antigen.

7. The method of claim 5, wherein the microbial antigen is an antigen derived from anthrax.

8. The method of claim 1, wherein the antigen is administered by administering a nucleic acid encoding the antigen.

9. The method of claim 1, wherein the host is a human.

10. The method of claim 2, wherein the method comprises administering two or more different antigens to the host.

11. The method of claim 2, wherein the antigen is a tumor antigen or microbial antigen.

12. The method of claim 2, wherein the antigen is an antigen derived from anthrax.

13. The method of claim 3, wherein the method comprises administering two or more different antigens to the host.

14. The method of claim 3, wherein the antigen is a tumor antigen or microbial antigen.

15. The method of claim 3, wherein the antigen is an antigen derived from anthrax.

16. The method of claim 2, wherein the antigen is a melanoma antigen.

17. The method of claim 3, wherein the antigen is a melanoma antigen.

18. A method of enhancing an antigen-specific immune response in a host comprising administering to the host an antigen and a polypeptide comprising HMGN1 (SEQ ID NO: 1), in an amount effective to enhance an antigen-specific immune response, wherein the antigen is derived from anthrax.

19. A method of enhancing the activation or recruitment of dendritic cells in a host comprising administering to the host an antigen and a polypeptide comprising HMGN1 (SEQ ID NO: 1), in an amount effective to enhance the activation or recruitment of dendritic cells in the host, wherein the antigen is derived from anthrax.

20. A method of shifting the Th-1/Th-2 balance of an immune response of a host towards a Th-1 type immune response comprising administering to the host an antigen and a polypeptide comprising HMGN1 (SEQ ID NO: 1), in an amount effective to shift the Th-1/Th-2 balance of an immune response towards a Th-1 type immune response, wherein the antigen is derived from anthrax.

21. The method of claim 18, wherein the method further comprises administering to the host one or more of HMGN3a (SEQ ID NO: 2), HMGN3b (SEQ ID NO: 3), HMGN4 (SEQ ID NO: 4), and Nsbp1 (SEQ ID NO: 5).

22. The method of claim 19, wherein the method further comprises administering to the host one or more of HMGN3a (SEQ ID NO: 2), HMGN3b (SEQ ID NO: 3), HMGN4 (SEQ ID NO: 4), and Nsbp1 (SEQ ID NO: 5).

23. The method of claim 20, wherein the method further comprises administering to the host one or more of HMGN3a (SEQ ID NO: 2), HMGN3b (SEQ ID NO: 3), HMGN4 (SEQ ID NO: 4), and Nsbp1 (SEQ ID NO: 5).

24. The method of claim 18, wherein the method comprises administering two or more different antigens to the host.

25. The method of claim 19, wherein the method comprises administering two or more different antigens to the host.

26. The method of claim 20, wherein the method comprises administering two or more different antigens to the host.

27. The method of claim 18, wherein the antigen is administered by administering a nucleic acid encoding the antigen.

28. The method of claim 19, wherein the antigen is administered by administering a nucleic acid encoding the antigen.

29. The method of claim 20, wherein the antigen is administered by administering a nucleic acid encoding the antigen.

30. The method of claim 18, wherein the host is a human.

31. The method of claim 19, wherein the host is a human.

32. The method of claim 20, wherein the host is a human.

* * * * *

SEQUENCE LISTING

```
<160> NUMBER OF SEQ ID NOS: 14

<210> SEQ ID NO 1
<211> LENGTH: 100
<212> TYPE: PRT
<213> ORGANISM: Homo sapiens

<400> SEQUENCE: 1

Met Pro Lys Arg Lys Val Ser Ser Ala Glu Gly Ala Ala Lys Glu Glu
1               5                   10                  15
```

```
Pro Lys Arg Arg Ser Ala Arg Leu Ser Ala Lys Pro Ala Lys Val
            20                  25                  30

Glu Ala Lys Pro Lys Ala Ala Lys Asp Lys Ser Asp Lys
        35                  40                  45

Lys Val Gln Thr Lys Gly Lys Arg Gly Ala Lys Gly Lys Gln Ala Glu
 50                  55                  60

Val Ala Asn Gln Glu Thr Lys Glu Asp Leu Pro Ala Glu Asn Gly Glu
 65                  70                  75                  80

Thr Lys Thr Glu Glu Ser Pro Ala Ser Asp Glu Ala Gly Leu Lys Glu
                    85                  90                  95

Ala Lys Ser Asp
            100

<210> SEQ ID NO 2
<211> LENGTH: 99
<212> TYPE: PRT
<213> ORGANISM: Homo sapiens

<400> SEQUENCE: 2

Met Pro Lys Arg Lys Ser Pro Glu Asn Thr Glu Gly Lys Asp Gly Ser
 1               5                  10                  15

Lys Val Thr Lys Gln Glu Pro Thr Arg Arg Ser Ala Arg Leu Ser Ala
                20                  25                  30

Lys Pro Ala Pro Pro Lys Pro Glu Pro Lys Pro Arg Lys Thr Ser Ala
            35                  40                  45

Lys Lys Glu Pro Gly Ala Lys Ile Ser Arg Gly Ala Lys Gly Lys Lys
        50                  55                  60

Glu Glu Lys Gln Glu Ala Gly Lys Glu Gly Thr Ala Pro Ser Glu Asn
 65                  70                  75                  80

Gly Glu Thr Lys Ala Glu Glu Ala Gln Lys Thr Glu Ser Val Asp Asn
                    85                  90                  95

Glu Gly Glu

<210> SEQ ID NO 3
<211> LENGTH: 77
<212> TYPE: PRT
<213> ORGANISM: Homo sapiens

<400> SEQUENCE: 3

Met Pro Lys Arg Lys Ser Pro Glu Asn Thr Glu Gly Lys Asp Gly Ser
 1               5                  10                  15

Lys Val Thr Lys Gln Glu Pro Thr Arg Arg Ser Ala Arg Leu Ser Ala
                20                  25                  30

Lys Pro Ala Pro Pro Lys Pro Glu Pro Lys Pro Arg Lys Thr Ser Ala
            35                  40                  45

Lys Lys Glu Pro Gly Ala Lys Ile Ser Arg Gly Ala Lys Gly Lys Lys
        50                  55                  60

Glu Glu Lys Gln Glu Ala Gly Lys Glu Gly Thr Glu Asn
 65                  70                  75

<210> SEQ ID NO 4
<211> LENGTH: 90
<212> TYPE: PRT
<213> ORGANISM: Homo sapiens

<400> SEQUENCE: 4

Met Pro Lys Arg Lys Ala Lys Gly Asp Ala Lys Gly Asp Lys Ala Lys
 1               5                  10                  15
```

Val Lys Asp Glu Pro Gln Arg Arg Ser Ala Arg Leu Ser Ala Lys Pro
            20                  25                  30

Ala Pro Pro Lys Pro Glu Pro Arg Pro Lys Lys Ala Ser Ala Lys Lys
        35                  40                  45

Gly Glu Lys Leu Pro Lys Gly Arg Lys Gly Lys Ala Asp Ala Gly Lys
    50                  55                  60

Asp Gly Asn Asn Pro Ala Lys Asn Arg Asp Ala Ser Thr Leu Gln Ser
65                  70                  75                  80

Gln Lys Ala Glu Gly Thr Gly Asp Ala Lys
            85                  90

<210> SEQ ID NO 5
<211> LENGTH: 282
<212> TYPE: PRT
<213> ORGANISM: Homo sapiens

<400> SEQUENCE: 5

Met Pro Lys Arg Lys Ala Ala Gly Gln Gly Asp Met Arg Gln Glu Pro
1               5                   10                  15

Lys Arg Arg Ser Ala Arg Leu Ser Ala Met Leu Val Pro Val Thr Pro
            20                  25                  30

Glu Val Lys Pro Lys Arg Thr Ser Ser Arg Lys Met Lys Thr Lys
        35                  40                  45

Ser Asp Met Met Glu Glu Asn Ile Asp Thr Ser Ala Gln Ala Val Ala
    50                  55                  60

Glu Thr Lys Gln Glu Ala Val Val Glu Glu Asp Tyr Asn Glu Asn Ala
65                  70                  75                  80

Lys Asn Gly Glu Ala Lys Ile Thr Glu Ala Pro Ala Ser Glu Lys Glu
            85                  90                  95

Ile Val Glu Val Lys Glu Glu Asn Ile Glu Asp Ala Thr Glu Lys Gly
            100                 105                 110

Gly Glu Lys Lys Glu Ala Val Ala Ala Glu Val Lys Asn Glu Glu Glu
            115                 120                 125

Asp Gln Lys Glu Asp Glu Glu Asp Gln Asn Glu Glu Lys Gly Glu Ala
    130                 135                 140

Gly Lys Glu Asp Lys Asp Glu Lys Gly Glu Glu Asp Gly Lys Glu Asp
145                 150                 155                 160

Lys Asn Gly Asn Glu Lys Gly Glu Asp Ala Lys Glu Lys Glu Asp Gly
            165                 170                 175

Lys Lys Gly Glu Asp Gly Lys Gly Asn Gly Glu Asp Gly Lys Glu Lys
            180                 185                 190

Gly Glu Asp Glu Lys Glu Glu Asp Arg Lys Glu Thr Gly Asp Gly
            195                 200                 205

Lys Glu Asn Glu Asp Gly Lys Glu Gly Asp Lys Lys Glu Gly Lys
    210                 215                 220

Asp Val Lys Val Lys Glu Asp Glu Lys Glu Arg Glu Asp Gly Lys Glu
225                 230                 235                 240

Asp Glu Gly Gly Asn Glu Glu Glu Ala Gly Lys Glu Lys Glu Asp Leu
            245                 250                 255

Lys Glu Glu Glu Glu Gly Lys Glu Glu Asp Glu Ile Lys Glu Asp Asp
            260                 265                 270

Gly Lys Lys Glu Glu Pro Gln Ser Ile Val
            275                 280

<210> SEQ ID NO 6
<211> LENGTH: 300

<212> TYPE: DNA
<213> ORGANISM: Homo sapiens

<400> SEQUENCE: 6

```
atgcccaaga ggaaggtcag ctccgccgaa ggcgccgcca aggaagagcc caagaggaga    60
tcggcgcggt tgtcagctaa acctcctgca aaagtggaag cgaagccgaa aaaggcagca   120
gcgaaggata atcttcaga caaaaaagtg caaacaaaag ggaaaagggg agcaaaggga   180
aaacaggccg aagtggctaa ccaagaaact aaagaagact tacctgcgga aaacggggaa   240
acgaagactg aggagagtcc agcctctgat gaagcaggag agaaagaagc caagtctgat   300
```

<210> SEQ ID NO 7
<211> LENGTH: 297
<212> TYPE: DNA
<213> ORGANISM: Homo sapiens

<400> SEQUENCE: 7

```
atgccgaaga gaaagtctcc agagaataca gagggcaaag atggatccaa agtaactaaa    60
caggagccca agacggtc tgccagattg tcagcgaaac ctgctccacc aaaacctgaa    120
cccaaaccaa gaaaaacatc tgctaagaaa gaacctggag caaagattag cagaggtgct   180
aaagggaaga aggaggaaaa gcaggaagct ggaaaggaag gtactgcacc atctgaaaat   240
ggtgaaacta agctgaaga ggcacagaaa actgaatctg tagataacga gggagaa      297
```

<210> SEQ ID NO 8
<211> LENGTH: 231
<212> TYPE: DNA
<213> ORGANISM: Homo sapiens

<400> SEQUENCE: 8

```
atgccgaaga gaaagtctcc agagaataca gagggcaaag atggatccaa agtaactaaa    60
caggagccca agacggtc tgccagattg tcagcgaaac ctgctccacc aaaacctgaa    120
cccaaaccaa gaaaaacatc tgctaagaaa gaacctggag caaagattag cagaggtgct   180
aaagggaaga aggaggaaaa gcaggaagct ggaaaggaag gcacagaaaa c           231
```

<210> SEQ ID NO 9
<211> LENGTH: 270
<212> TYPE: DNA
<213> ORGANISM: Homo sapiens

<400> SEQUENCE: 9

```
atgcccaaga gaaaggcaaa aggagatgct aaaggtgata agcaaaggt gaaggatgag    60
ccacagagga gatcagctcg gttgtctgct aaaccagctc ctccaaaacc agagcccagg   120
cctaaaaagg cctctgcaaa gaaggagag aagcttccca aagggagaaa ggggaaagca   180
gatgctggaa aggatgggaa caaccctgca aaaaaccgag atgcctctac actccagtcc   240
cagaaagcgg aaggcactgg ggatgccaag                                    270
```

<210> SEQ ID NO 10
<211> LENGTH: 846
<212> TYPE: DNA
<213> ORGANISM: Homo sapiens

<400> SEQUENCE: 10

```
atgcccaaaa gaaaggctgc aggtcaaggt gatatgaggc aggagccaaa gagaagatct    60
gccaggttgt ctgctatgct tgtgccagtt acaccagagg tgaagcctaa agaacatca   120
agttcaagga aaatgaagac aaaaagtgat atgatggaag aaaacataga tacaagtgcc   180
```

-continued

```
caagcagttg ctgaaaccaa gcaagaagca gttgttgaag aagactacaa tgaaaatgct    240
aaaaatggag aagccaaaat tacagaggca ccagcttctg aaaagaaat tgtggaagta     300 aaagaagaaa atattgaaga tgccacagaa aagggaggag aaaagaaaga agcagtggca    360
gcagaagtaa aaatgaaga agaagatcag aaagaagatg aagaagatca aaacgaagag    420
aaaggggaag ctggaaaaga agacaaagat gaaaaagggg aagaagatgg aaaagaggat    480
aaaaatggaa atgagaaagg agaagatgca aaagagaaag aagatggaaa aaaaggtgaa    540
gacggaaaag gaaatggaga agatggaaaa gagaaaggag aagatgaaaa agaggaagaa    600
gacagaaaag aaacaggaga tggaaaagag aatgaagatg gaaagagaa gggagataaa    660 aaagagggga agatgtaaa agtcaagaa gatgaaaaag agagaagaa tggaaaagaa    720 gatgaaggtg gaaatgagga agaagctgga aagagaaag aagatttaaa agaagaggaa    780
gaaggaaaag aggaagatga gatcaaagaa gatgatggaa aaaaagagga gccacagagt    840
attgtt                                                               846
```

<210> SEQ ID NO 11
<211> LENGTH: 36
<212> TYPE: PRT
<213> ORGANISM: Homo sapiens

<400> SEQUENCE: 11

Lys Glu Glu Pro Lys Arg Arg Ser Ala Arg Leu Ser Ala Lys Pro Pro
1               5                   10                  15

Ala Lys Val Glu Ala Lys Pro Lys Lys Ala Ala Ala Lys Asp Lys Ser
            20                  25                  30

Ser Asp Lys Lys
        35

<210> SEQ ID NO 12
<211> LENGTH: 30
<212> TYPE: PRT
<213> ORGANISM: Homo sapiens

<400> SEQUENCE: 12

Lys Gln Glu Pro Thr Arg Arg Ser Ala Arg Leu Ser Ala Lys Pro Ala
1               5                   10                  15

Pro Pro Lys Pro Glu Pro Lys Pro Arg Lys Thr Ser Ala Lys
            20                  25                  30

<210> SEQ ID NO 13
<211> LENGTH: 30
<212> TYPE: PRT
<213> ORGANISM: Homo sapiens

<400> SEQUENCE: 13

Lys Asp Glu Pro Gln Arg Arg Ser Ala Arg Leu Ser Ala Lys Pro Ala
1               5                   10                  15

Pro Pro Lys Pro Glu Pro Arg Pro Lys Lys Ala Ser Ala Lys
            20                  25                  30

<210> SEQ ID NO 14
<211> LENGTH: 30
<212> TYPE: PRT
<213> ORGANISM: Homo sapiens

<400> SEQUENCE: 14

-continued

```
Lys Arg Arg Ser Ala Arg Leu Ser Ala Met Leu Val Pro Val Thr Pro
1               5                   10                  15

Glu Val Lys Pro Lys Arg Thr Ser Ser Ser Arg Lys Met Lys
                20                  25              30
```